(12) United States Patent
Miller et al.

(10) Patent No.: US 7,186,892 B2
(45) Date of Patent: *Mar. 6, 2007

(54) EXPRESSION OF SEDOHEPTULOSE 1,7 BISPHOSPHATASE IN TRANSGENIC PLANTS

(75) Inventors: Philip W. Miller, Ballwin, MO (US); Robin L. Staub, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 11 days.

This patent is subject to a terminal disclaimer.

(21) Appl. No.: 10/901,663

(22) Filed: Jul. 29, 2004

(65) Prior Publication Data

US 2005/0005331 A1    Jan. 6, 2005

(51) Int. Cl.
*C12N 15/82* (2006.01)
*A01H 5/00* (2006.01)

(52) U.S. Cl. .................. 800/298; 800/284; 800/320.1

(58) Field of Classification Search .................. None
See application file for complete search history.

(56) References Cited

U.S. PATENT DOCUMENTS 6,815,580 B1 * 11/2004 Miller et al. ................ 800/284

FOREIGN PATENT DOCUMENTS

WO    WO 96/21737    *    7/1996

OTHER PUBLICATIONS

Lazar et al, 1988, Mol. Cell. Biol. 8:1247-1252.*
Hill et al, 1998, Biochem. Biophys. Res. Comm. 244:573-577.*
Guo et al, 2004, Proc. Natl. Acad. Sci. USA 101: 9205-9210.*
Dunford et al, 1998, Photosyn. Res. 58:221-230.*
Raines et al, 1999, J. Exp. Bot. 50:1-8.*
Yoo et al, 1995, Curr. Microbiol. 31:55-61.*
Willingham et al, 1994, Plant Mol. Biol. 26:1191-1200.*
Raines et al, 1992, Eur. J. Biochem. 205:1053-1059.*
Hahn et al, 1994, Plant Physiol. 104:1101-1102.*
Hahn, 1998, Plant Mol. Biol. 36:929-934.*

* cited by examiner

*Primary Examiner*—Anne Kubelik
(74) *Attorney, Agent, or Firm*—Thomas E Kelley

(57) ABSTRACT

Sedoheptulose 1,7-bisphosphatase (SBPase) is an enzyme catalyzing the reaction converting sedoheptulose 1,7-bisphosphate into sedoheptulose 7-phosphate. This enzyme is located in the chloroplast in leaves and stems. Overexpression of SBPase in transgenic plants is provided to improve plant yield by increasing leaf starch biosynthetic ability in particular and sucrose production in general. Deregulated variants of the enzymes are also provided.

3 Claims, 11 Drawing Sheets

Figure 8. Immunoblot of wheat sedoheptulose-1,7-bisphosphatase expressed in corn protoplasts.
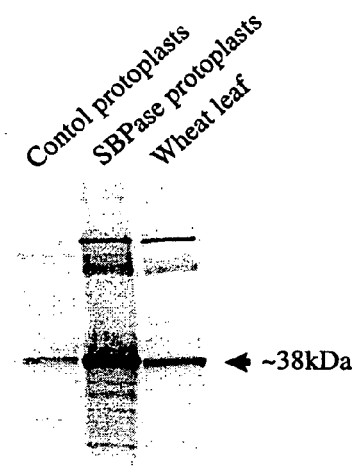

Figure 9. Sedoheptulose-1,7-bisphosphatase activity.
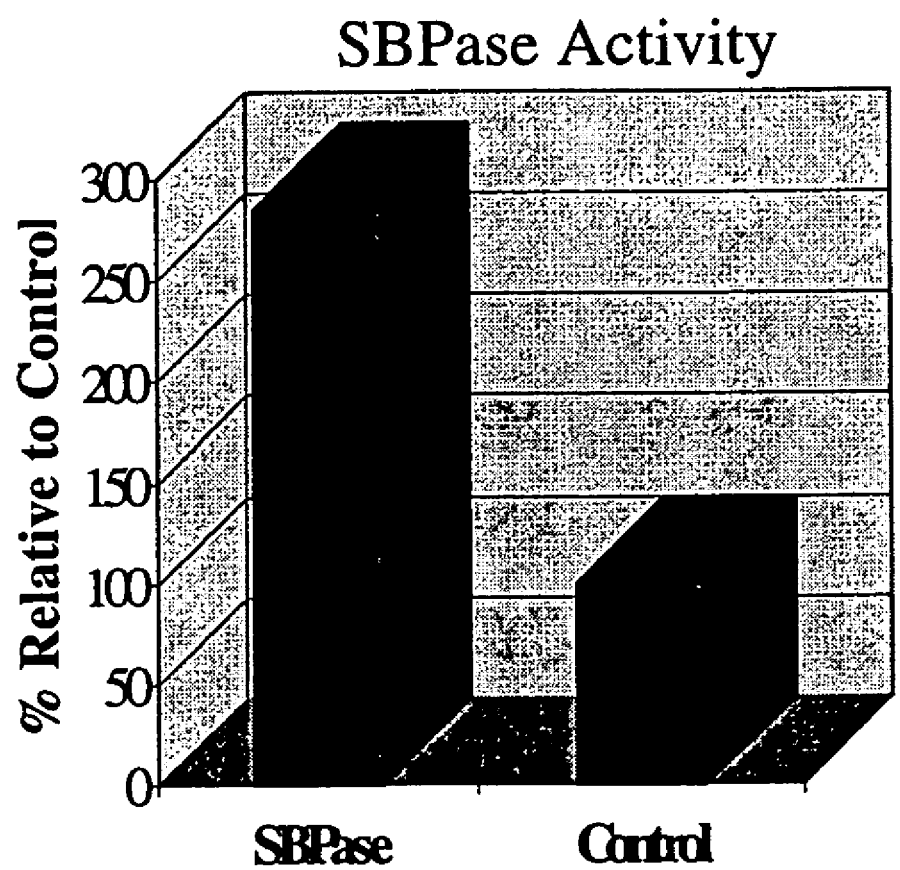

Figure 10A.  Alignment of Sedoheptulose-1,7-bisphosphatase Proteins

```
                   1                                                        50
SEQ ID NO:23       ----------  --MQATAVAT  AAPAARVATT  GKAATGVKAA  PRVAVRAAGA
SEQ ID NO:24       ----MAAMMM  RQKVAGATAG  ERRSAVAPKM  GRAAT----A  P-VVVASANA
SEQ ID NO:25       MET-SMACCS  RSIVLPRVSP  QHSSALV--P  S---SINLKS  LK-SSSLFGE
SEQ ID NO:26       MET-SIACYS  RGILPPSVSS  QRSSTLVSPP  SYSTSSSFKR  LK-SSSIFGD
SEQ ID NO:27       METVAAAGYA  HG------AA  TRSPACCAAM  SFSQSYRPKA  ARPATSFYGE 51                                                      100
SEQ ID NO:23       SASSSFATGA  RL--SAKASR  TAARRAAVAA  QAKIGDTLEE  FLLEATPDPK
SEQ ID NO:24       SAFKGAAVTA  RVKASTRAAR  VQSRRTAVLT  QAKIGDSLAE  FLVEATPDPK
SEQ ID NO:25       SLRM-TTKSS  --V---RVNK  AKN--SSLVT  KCELGDSLEE  FLAKATTDKG
SEQ ID NO:26       SLRL-APKSQ  --L---KATK  AKSNGASTVT  KCEIGQSLEE  FLAQATPDKG
SEQ ID NO:27       SLRANTARTS  --FPAGRQSK  AASR-AALTT  RCAIGDSLEE  FLTKATPDKN 101                                                     150
SEQ ID NO:23       LRQLMMSMSE  AIRTIAYKVR  TASCGGTACV  NSFGDEQLAV  DLLADKLLFE
SEQ ID NO:24       LRHVMMSMAE  ATRTIAHKVR  TASCAGTACV  NSFGDEQLAV  DMVADKLLFE
SEQ ID NO:25       LIRLMMCMGE  ALRTIGFKVR  TASCGGTQCV  NTFGDEQLAI  DVLADKLLFE
SEQ ID NO:26       LRTLLMCMGE  ALRTIAFKVR  TASCGGTACV  NSFGDEQLAV  DMLADKLLFE
SEQ ID NO:27       LIRLLICMGE  AMRTIAFKVR  TASCGGTACV  NSFGDEQLAV  DMLADKLLFE 151                                                     200
SEQ ID NO:23       ALKYSGCCKL  ACSEEVPEPL  DLGGE---GF  SVAFDPLDGS  SIVDTNFSVG
SEQ ID NO:24       ALKYSHVCKL  ACSEEVPEPV  DMGGE---GF  CVAFDPLDGS  SSSDTNFAVG
SEQ ID NO:25       ALNYSHFCKY  ACSEELPELQ  DMGGPVDGGF  SVAFDPLDGS  SIVDTNFSVG
SEQ ID NO:26       ALQYSHVCKY  ACSEEVPELQ  DMGGPVEGGF  SVAFDPLDGS  SIVDTNFTVG
SEQ ID NO:27       ALEYSHVCKY  ACSEEVPELQ  DMGGPVEGGF  SVAFDPLDGS  SIVDTNFTVG 201                                                     250
SEQ ID NO:23       TIFGVWPSDK  LTGITGRQQA  AAGMGIYGPR  TVFCIALKDA  PGCHEFLLQD
SEQ ID NO:24       TIFCVWPSDK  LTNITGREQV  AAGMGIYGPR  TVFCIALKDA  PGCHEFLLMD
SEQ ID NO:25       TIFGVWPSDK  LTGVTGRDQV  AAAMGIYGPR  TTYVLALKDY  PGTHEFLLLD
SEQ ID NO:26       TIFGVWPSDK  LTGTTGGDQV  AAAMGIYGPR  TTYVLAVKGF  PGTHEFLLLD
SEQ ID NO:27       TIFGVWPSDK  LTGVTGGDQV  AAAMGIYGPR  TTFVVALKDC  PGTHEFLLLD 251                                                     300
SEQ ID NO:23       DGKWLHVKET  ETIGEGKMFS  PGNLRATFDN  PAYEKLIAYY  IGEKYTLRYT
SEQ ID NO:24       DGKWMHVKET  THIGEGKMFA  PGNLRATFDN  PAYERLINFY  LGEKYTLRYT
SEQ ID NO:25       EGKWQHVKET  TEINEGKLFC  PGNLRATSDN  ADYAKLIQYY  IKEKYTLRYT
SEQ ID NO:26       EGKWQHVKET  TEIAEGKMFS  PGNLRATFDN  SEYSKLIDYY  VKEKYTLRYT
SEQ ID NO:27       EGKWQHVKDT  TSIGEGKMFS  PGNLRATFDN  PDYDKLVNYY  VKEKYTLRYT 301                                                     350
SEQ ID NO:23       GGMVPDVFQI  IVKEKGVFTN  VISPSTKAKL  RLLFEVAPLA  LLVEKAGGAS
SEQ ID NO:24       GGIVPDLFQI  IVKEKGVFTN  LTSPTTKAKL  RILFEVAPLA  LLIEKAGGAS
SEQ ID NO:25       GGMVPDVNQI  IVKEKGIFTN  VISPTAKAKL  RLLFEVAPLG  FLIEKAGGHS
SEQ ID NO:26       GGMVPDVNQI  IVKEKGIFTN  VTSPTAKAKL  RLLFEVAPLG  LLIENAGGFS
SEQ ID NO:27       GGMVPDVNQI  IVKEKGIFTN  VTSPTAKAKL  RLLFEVAPLG  FLIEKAGGHS
```

Figure 10B. Alignment of Sedoheptulose-1,7-bisphosphatase Proteins

```
              351                                                        400
SEQ ID NO:23  SCDGLCVSGL DVEVKQHDQR TQICYGSKGD VRRFEEYMYG NSPRFSEVTA
SEQ ID NO:24  SCDGKAVSAL DIPILVCDQR TQICYGSIGE VRRFEEYMYG TSPRFSEKVV
SEQ ID NO:25  S-EGT-KSVL DIEVKNLDDR TQVAYGSLNE IIRFEKTLYG SS-RLEEPVP
SEQ ID NO:26  S-DGH-KSVL DKTIINLDDR TQVAYGSKNE IIRFEETLYG TS-RLKN-VP
SEQ ID NO:27  S-DGK-QSVL DKVISVLDER TQVAYGSKNE IIRFEETLYG SS-RLAASAT

401
SEQ ID NO:23  -----
SEQ ID NO:24  A----
SEQ ID NO:25  VGAAA
SEQ ID NO:26  IGVTA
SEQ ID NO:27  VGATA
```

EXPRESSION OF SEDOHEPTULOSE 1,7 BISPHOSPHATASE IN TRANSGENIC PLANTS

This application claims priority of the U.S. provisional application, Ser. No. 60/133,964, filed on May 13, 1999.

FIELD OF THE INVENTION

This invention relates to the expression of sedoheptulose 1,7 bisphosphatase (SBPase) in transgenic plants to increase or improve plant growth and development, yield, vigor, and distribution of carbon assimilates. Transgenic plants expressing SBPase have improved carbon assimilation, export and storage in plant source and sink organs, which results in growth, yield and quality improvements in crop plants.

BACKGROUND OF THE INVENTION

Recent advances in genetic engineering have provided the prerequisite tools to transform plants to contain alien (often referred to as "heterogenous or heterologous") or improved endogenous genes. The introduction of such a gene in a plant would desirably lead to an improvement of an already existing pathway in plant tissues or introduction of a novel pathway to modify desired product levels, increase metabolic efficiency, and/or save on energy cost to the cell. It is presently possible to produce plants with unique physiological and biochemical traits and characteristics of high agronomic and crop processing importance. Traits that play an essential role in plant growth and development, crop yield potential and stability, and crop quality and composition are particularly desirable targets for crop plant improvement. These improvements may be achieved by genetically modifying a crop plant for improved carbon assimilation, more efficient carbon storage, and/or increased carbon export and partitioning capabilities.

Atmospheric carbon fixation (photosynthesis) by plants, algae, and photosynthetic bacteria represents the major source of energy to support processes in such organisms. The Calvin cycle, located in the stroma of the chloroplast, is the primary pathway of carbon assimilation in higher plants. Carbon assimilates can either leave the cycle for sucrose or starch biosynthesis or continue through the cycle to regenerate the carbon acceptor molecule, ribulose-1,5-bisphosphate. Sedoheptulose-1,7-bisphosphatase is an enzyme that catalyzes an essentially irreversible reaction in the branch region where intermediates can leave the cycle, and therefore it may be essential to regulating carbon partitioning between the regeneration phase of the cycle and sucrose and starch biosynthesis.

SBPase has no known cytosolic counterpart and is reported to be found only in the chloroplast, where it dephosphorylates sedoheptulose-1,7-bisphosphate (SBP) to form sedoheptulose-7-phosphate and inorganic phosphate. This enzyme is specific for SBP and is inhibited by its products as well as glycerate (Schimkat et al., 1990) and fructose-2,6-bisphosphate (Cadet and Meunier, 1988b). Light, a reducing agent, and $Mg^{2+}$ are required for activity (Woodrow, 1982; Cadet and Meunier, 1988a). The enzyme is a homodimer with a subunit molecular mass of 35–38 kDa (Nishizawa and Buchanan, 1981; Cadet and Meunier, 1988c).

It has been reported that removal of more than 80% of the enzymatic activity of SBPase in tobacco plants using antisense technology resulted in chlorosis, reduced growth rates, and reduced carbon assimilate levels (Harrison et al., 1998). Reduction in the quantum efficiency of photosystem II was also observed, which resulted in the reduction in carbohydrate content of the leaves. Analysis of carbohydrate status showed a shift from starch while sucrose levels were maintained. These results indicate that SBPase is a potential rate-limiting step in carbohydrate metabolism.

Various sedoheptulose 1,7-bisphosphatases have been characterized biochemically, and the corresponding mRNAs (CDNA) have been cloned from an alga (Genbank accession number: X74418; Hahn and Kuck, 1994) and some higher plants such as *Triticum aestivum* (Genbank accession number: X65540; Miles et al., 1993), *Spinacia oleracea* (Genbank accession number: L76556; Martin et al., 1996) and *Arabidopsis thaliana* (Genbank accession number: S74719; Willingham, et al., 1994). Thus, over-expression of a nucleic acid sequence encoding SBPase in a transgenic plant will provide advantageous results in the plant such as improved carbon assimilation, export and storage; increased photosynthetic capacity; and extended photosynthetic ability.

SUMMARY OF THE INVENTION

The present invention provides a method for improving the assimilation of carbon in plants using structural nucleic acid constructs that encode a sedoheptulose 1,7-bisphosphatase (SBPase) enzyme.

In accomplishing the foregoing, there is provided, in accordance with one aspect of the present invention, a method for improving the assimilation of carbon in a plant comprising the steps of:
 (a) inserting into the genome of a plant a nucleic acid sequence comprising in the 5' to 3' direction and operably linked,
  (i) a promoter that functions in the cells of a selected plant tissue,
  (ii) a structural nucleic acid sequence that causes the production of a sedoheptulose 1,7-bisphosphatase enzyme,
  (iii) a 3' non-translated nucleic acid sequence that functions in plant cells to cause transcriptional termination and the addition of polyadenylated nucleotides to the 3' end of a RNA sequence;
 (b) obtaining transformed plant cells containing the nucleic acid of step (a); and
 (c) regenerating from transformed plant cells a transformed plant that overexpresses the sedoheptulose 1,7-bisphosphatase enzyme in the plant cells.

In a further embodiment of the present invention an isolated nucleic acid sequence comprising a promoter capable of functioning in a plant cell, a structural nucleic acid sequence in sense orientation capable of causing the production of a sedoheptulose 1,7-bisphosphatase enzyme, and a 3' non-translated nucleic acid sequence capable of causing transcriptional termination and the addition of polyadenylated nucleotides to the 3' end of the transcribed MRNA sequence, is provided. This nucleic acid sequence may optionally include introns, 5' untranslated leader sequences or other nucleic acid sequences designed to enhance transcription and/or translation.

In a still further embodiment of the invention, a novel, isolated nucleic acid sequence encoding a sedoheptulose 1,7-bisphosphatase enzyme from a green algae, *Chlorella sorokiniana*, is provided.

In a yet further embodiment of the present invention, a variant nucleic acid sequence encoding a sedoheptulose 1,7-bisphosphatase enzyme is provided whereby the cysteine residues in the polypeptide sequence are modified to another amino acid in a manner providing an active enzyme regardless of the presence of light.

Therefore, in accordance with the present invention, a means for improving carbon assimilation, storage and export in the source tissues of a plant is provided. Further means of improved carbon accumulation in sinks (such as roots, tubers, seeds, stems, and bulbs) are provided, thus increasing the size of various sinks (larger roots and tubers) and subsequently increasing yield. The increased carbon availability to these sinks would improve and/or alter the composition of the cellular components of the plant (e.g., oils, proteins, starch and sucrose production and solids uniformity). One aim of the present invention is to overexpress sedoheptulose 1,7-bisphosphatases in plants by introducing a heterologous source of the sedoheptulose 1,7-bisphosphatase into the plant or by increasing the expression of the endogenous form of the gene in the plant.

Various advantages may be achieved by the aims of the present invention. Increasing the expression of the sedoheptulose 1,7-bisphosphatase enzyme in the chloroplast would increase the flow of carbon through the Calvin Cycle and potentially increase atmospheric carbon assimilation in the presence of light . This would result in an increase in photosynthetic efficiency, an increase in chloroplast starch production (a leaf carbon storage form degraded during periods when photosynthesis is low or absent), and an increase in sucrose production by the leaf resulting in a net increase in carbon export to the sink and developing tissues would be expected during a given photoperiod. This increase in source capacity is a desirable trait in crop plants and would lead to increased plant growth, storage ability, yield and vigor.

BRIEF DESCRIPTION OF THE DRAWINGS

FIG. 8 shows an immunoblot of SBPase protein expression in corn protoplasts transformed with pMON47203.

FIG. 9 shows a bar graph comparing SBPase activity in corn protoplasts expressing wheat SBPase with control protoplasts.

FIG. 10 shows an alignment of Sedoheptulose-1,7-bisphosphatase proteins.

DESCRIPTION OF SEQUENCES

Figure 1:
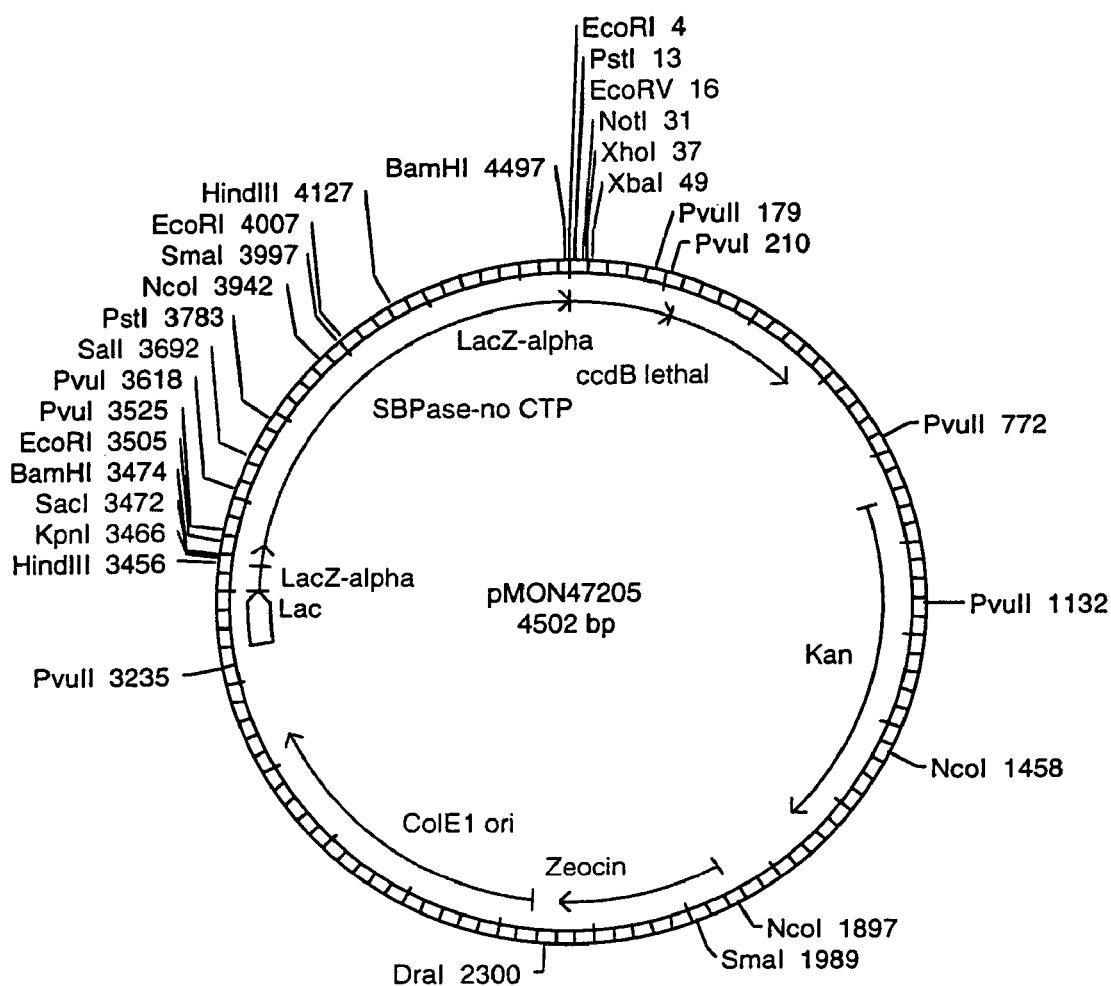
FIG. 1 shows a plasmid map for cloning vector pMON47205.

SEQ ID NO:1 synthetic primer
SEQ ID NO:2 synthetic primer
SEQ ID NO:3 DNA sequence for mature SBPase (no CTP)
SEQ ID NO:4 synthetic primer
SEQ ID NO:5 adaptor primer
SEQ ID NO:6 synthetic primer
SEQ ID NO:7 adaptor primer
SEQ ID NO:8 DNA sequence of SBPase with CTP
SEQ ID NO:9 amino acid sequence of SBPase
SEQ ID NO:10 a degenerate primer
SEQ ID NO:11 a gene-specific primer
SEQ ID NO:12 a predicted amino acid sequence
SEQ ID NO:13 a gene-specific primer
SEQ ID NO:14 a nested gene-specific primer
SEQ ID NO:15 a gene-specific primer
SEQ ID NO:16 a gene-specific primer
SEQ ID NO:17 a nested gene-specific primer
SEQ ID NO:18 a gene-specific primer
SEQ ID NO:19 a vector-specific primer
SEQ ID NO:20 the full length *Chlorella sorokiniana* SBPase cDNA sequence
SEQ ID NO:21 a mutagenic primer to change cysteines 110 and 115 to serines in *Chlorella sorokiniana* SBPase.
SEQ ID NO:22 a variant cDNA sequence in which cysteines 110 and 115 of *Chlorella sorokiniana* SBPase are changed to serines.
SEQ ID NO: 23 a predicted variant protein sequence of *Chlorella sorokiniana* SBPase in which cysteines 110 and 115 are changed to serines.

DETAILED DESCRIPTION OF THE INVENTION

The following definitions are provided in order to aid those skilled in the art in understanding the detailed description of the present invention.

The term "identity"refers to amino acid or nucleic acid sequences that when compared using the local homology algorithm of Smith and Waterman (1981)) in the BestFit program (Wisconsin Package Version 10.0, Genetics Computer Group (GCG), Madison, Wis.) are exactly alike.

The term "similarity"refers to amino acid sequences that when compared using the local homology algorithm of Smith and Waterman (1981) in the BestFit program (Wisconsin Package Version 10.0, Genetics Computer Group (GCG), Madison, Wis.) match when conservative amino acid substitutions are considered.

"C-terminal region" refers to the region of a peptide, polypeptide, or protein chain from the middle thereof to the end that carries the amino acid having a free carboxyl group.

The phrase "nucleic acid or DNA segment heterologous to the promoter region" means that the coding DNA or nucleic acid segment does not exist in nature with the promoter to which it is now operably linked or coupled therewith.

The term "encoding DNA" refers to chromosomal DNA, plasmid DNA, cDNA, or synthetic DNA that encodes any of the enzymes discussed herein.

The term "genome" as it applies to bacteria encompasses both the chromosome and plasmids within a bacterial host cell. Encoding DNAs of the present invention introduced into bacterial host cells can therefore be either chromosomally integrated or plasmid-localized. The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized.

The terms "microbe" or "microorganism" refer to algae, bacteria, fungi, and protozoa.

The term "mutein" refers to a mutant form of a peptide, polypeptide, or protein.

"N-terminal region" refers to the region of a peptide, polypeptide, or protein chain from the amino acid having a free amino group to the middle of the chain.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region.

This invention is directed to a method for producing plant cells demonstrating an increased or improved plant growth and development, yield and vigor. The method utilizes a DNA sequence encoding an sbpase (sedoheptulose 1,7-bisphosphatase) gene integrated in the cellular genome of a plant as the result of genetic engineering and causes expression of the SBPase enzyme. Plants that overexpress the SBPase enzyme and that have improved carbon assimilation, export and storage in plant source and sink organs, which results in growth, yield, and quality improvements are also contemplated in this invention.

The mechanism whereby the expression of exogenous SBPase modifies carbon relationships derives from source-sink relationships. The leaf tissue is a sucrose source, and if more sucrose, resulting from the activity of increased SBPase expression, is transported to a sink it results in increased storage carbon (sugars, starch, etc.) per given weight of the sink tissue.

A method for producing genetically transformed plants that express increased levels of SBPase requires the introduction of a double-stranded recombinant DNA molecule into the nuclear genome of a plant cell. The DNA molecule must (1) contain a structural DNA for the SBPase enzyme being introduced into the plant cell; (2) possess a promoter that functions in plants to regulate the production of an RNA sequence in a constitutive or tissue-specific manner by RNA polymerase enzyme; and (3) have a 3'-untranslated region that functions to cause transcriptional termination and the addition of polyadenylated nucleotides to the 3' end of the RNA. The resulting primary RNA molecule is subsequently processed in the nucleus, a process that involves the removal of intronic sequences and the addition of polyadenylate nucleotides to the 3' end of the MRNA.

Sedoheptulose 1,7-bisphosphatases

As used herein, the term "sedoheptulose 1,7-bisphosphatase" means an enzyme (E.C. 3.1.3.37) that catalyzes the dephosphorylation of sedoheptulose 1,7-bisphosphae bisphosphate to sedoheptulose 7-phosphate and inorganic phosphate.

The SBPase gene used in the DNA constructs of the present invention can be any SBPase gene. Numerous SBPase cDNA sequences are known in the art including the sequences from wheat (Raines et al., 1992), spinach (Martin et al., 1996), *Arabidopsis* (Willingham et al., 1994), and *Ralstonia* (Yoo and Bowien, 1995) The examples provided herein are illustrative of the use an SBPase, and should not be interpreted in any way to limit the scope of the present invention. Individuals skilled in the art will recognize that various other genes as well as alterations can be made to genes and methods described herein while not departing from the spirit and scope of the present invention. For example, one could utilize a SBPase that has been selected from alternative organisms or that has been modified to lack or alter enzymatic feedback inhibition by orthophosphate and glycerate. Because SBPase is activated by thioredoxin or DTT, one could also use mutagenesis to manipulate the enzyme to remain in the activated state without the reducer present. These mutated forms can then be utilized to modify plant metabolism as well. The overproduction of carbohydrate may also provide an increase in tolerance to stresses that affect the water potential of the plants by providing more carbon skeletons. Further means of improved carbon accumulation in sinks (such as roots, tubers, seeds, stems, and bulbs) are provided, thus increasing the size of various sinks (larger roots and tubers) and subsequently increasing yield. The increased carbon availability to these sinks would improve cellular component composition (e.g., oil, protein, starch and sucrose production and solids uniformity). Thus, many different nucleic acid sequences that encode a sedoheptulose 1,7-bisphosphatase activity may be isolated and used in the present invention.

The SBPase cDNA from *Chlorella sorokiniana* is identified herein and may advantageously be used in connection with this invention. This gene may also be deregulated with respect to light by alteration of the cysteine residues to another amino acid, e.g., serine. Preferably, any cDNA sequence encoding SBPase that is about 85% identical to the *Chlorella sorokiniana* cDNA is within the scope of this invention, more preferably such cDNA sequence that is about 90% identical to the *Chlorella sorokiniana* cDNA, and most preferably about 95% identical to the *Chlorella sorokiniana* cDNA. Moreover, any amino acid sequence encoding SBPase that is about 85%, and more preferably about 90% similar to the *Chlorella sorokiniana* predicted amino acid sequence disclosed herein is considered within the scope of this invention.

Bisphosphatase genes from the facultative chemoautotroph *Alcaligenes eutrophus* (now named *Ralstonia eutropha*) and from the algae *Synechococcus lepoliensis* encode proteins with a dual activity, FBPase and SBPase, in the Calvin cycle (Yoo and Bowien, 1995; Gerbling et al., 1986). Genes encoding proteins with SBPase activity can be cloned from these or other organisms by anyone skilled in the art using well established methods. The source of the SBPase genes for use in this invention as described is not limited to the organisms described above and should not be interpreted in any way to limit the scope of the present invention. In one embodiment of the invention, the SBPase gene may be fused to a chloroplast transit peptide, in order to target the SBPase protein to the plastid. Those skilled in the art will also recognize that various other chimeric constructs can be made that utilize the functionality of a particular plastid transit peptide to import the sedoheptulose-1,7-bisphosphatase enzyme into the plant cell plastid depending on the promoter tissue specificity.

Gene Construction and Modifications

A sedoheptulose 1,7 bisphosphatase enzyme considered in this invention includes any sequence of amino acids, such as protein, polypeptide, or peptide fragment, that demonstrates the ability to catalyze the dephosphorylation of sedoheptulose 1,7-bisphosphate to sedoheptulose 7-phosphate and inorganic phosphate. As described above, these can be sequences obtained from a heterologous source, such as algae, bacteria, fungi, and protozoa, or endogenous plant sequences, by which is meant any sequence that can be naturally found, in a plant cell, including native (indigenous) plant sequences as well as sequences from plant viruses or plant pathogenic bacteria.

It will be recognized by one of ordinary skill in the art that SBPase enzyme gene sequences may also be modified using standard techniques such as sitespecific mutation or PCR, or modification of the sequence may be accomplished by producing a synthetic nucleic acid sequence and will still be considered a SBPase enzyme nucleic acid sequence of this invention. For example, wobble positions in codons may be changed such that the nucleic acid sequence encodes the same amino acid sequence, or alternatively, codons can be altered such that conservative or nonconservative amino acid substitutions result. In either case, the peptide or protein maintains the desired enzymatic activity and is thus considered part of this invention.

In one embodiment of the invention, the SBPase nucleic acid sequence is modified to change cysteine residues in the amino acid sequence to a different amino acid to prevent formation of disulfide bridges in the mature polypeptide between the cysteine residues providing an active enzyme regardless of the presence of light and also therefore prevent inactivation of the native protein by oxidation. For example, in the wheat SBPase, the cysteine residues at positions 52 and 57 (numbers correspond to mature wheat SBPase as described in Raines et al. (1999) are modified to a different amino acid such as a serine, alanine or glycine to prevent formation of the disulfide bond there between. Correspondingly, the cysteine residues at amino acid positions 110 and 115 of the *Chlorella* SBPase (corresponding to the *Chlorella* SBPase numbering in SEQ ID NO:12) would also be modified for the same effect.

A nucleic acid sequence to a SBPase enzyme may be a DNA or RNA sequence, derived from genomic DNA, cDNA, MRNA, or may be synthesized in whole or in part. The structural gene sequence may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene may be synthesized using codons preferred by a selected plant host. Plant-preferred codons may be determined, for example, from the codons used most frequently in the proteins expressed in a particular plant host species. Other modifications of the gene sequences may result in mutants having slightly altered activity.

If desired, the gene sequence of the sbpase gene can be changed without changing the protein/amino acid sequence in such a manner as may increase expression and thus even more positively affect carbohydrate content in transformed plants. A preferred manner for making the changes in the sbpase gene sequence are set out in PCT Publication WO 90/10076. A gene synthesized by following the methodology set out therein may be introduced into plants as described below and result in higher levels of expression of the SBPase enzyme. This may be particularly useful in monocots such as maize, rice, wheat, sugarcane and barley.

Promoters

A number of promoters that are active in plant cells have been described in the literature. These include the nopaline synthase (NOS) and octopine synthase (OCS) promoters (which are carried on tumor-inducing plasmids of *Agrobacterium tumefaciens*), the caulimovirus promoters such as the cauliflower mosaic virus (CaMV) 19S and 35S and the figwort mosaic virus (FMV) 35S-promoters, the light-inducible promoter from the small subunit of ribulose-1,5-bisphosphate carboxylase (ssRUBISCO), a very abundant plant polypeptide, and the chlorophyll a/b binding protein gene promoters, etc. All of these promoters have been used to create various types of DNA constructs that have been expressed in plants; see, e.g., PCT publication WO 84/02913.

Promoters that are known to or are found to cause transcription of DNA in plant cells can be used in the present invention. Such promoters may be obtained from a variety of sources such as plants and plant viruses and include, but are not limited to, the enhanced CaMV35S promoter and promoters isolated from plant genes such as ssRUBISCO genes. It is preferred that the particular promoter selected should be capable of causing sufficient expression to result in the production of an effective amount of sedoheptulose 1,7-bisphosphatase enzyme to cause the desired increase in carbon assimilation, export and storage. Expression of the double-stranded DNA molecules of the present invention can be driven by a constitutive promoter, expressing the DNA molecule in all or most of the tissues of the plant. In addition, it may also be preferred to bring about expression of the sbpase gene in specific tissues of the plant, such as leaf or stem, and the promoter chosen should have the desired tissue and developmental specificity. Those skilled in the art will recognize that the amount of sedoheptulose 1,7-bisphosphatase needed to induce the desired increase in carbon assimilation, export, or storage may vary with the type of plant. Therefore, promoter function should be optimized by selecting a promoter with the desired tissue expression capabilities and approximate promoter strength and selecting a transformant that produces the desired sedoheptulose 1,7-bisphosphatase activity or the desired change in metabolism of carbohydrates in the target tissues. This selection approach from the pool of transformants is routinely employed in expression of heterologous structural genes in plants because there is variation between transformants containing the same heterologous gene due to the site of gene insertion within the plant genome (commonly referred to as "position effect"). In addition to promoters that are known to cause transcription (constitutively or tissue-specific) of DNA in plant cells, other promoters may be identified for use in the current invention by screening a plant cDNA library for genes that are selectively or preferably expressed in the target tissues and then determine the promoter regions.

For the purpose of expressing the sbpase gene in source tissues of the plant, such as the leaf or stem, it is preferred that the promoters utilized in the double-stranded DNA molecules of the present invention have increased expression in these specific tissues. For this purpose, one may choose from a number of promoters for genes with leaf-specific or leaf-enhanced expression. Examples of such genes known from the literature are the chloroplast glutamine synthetase GS2 from pea (Edwards et al., 1990), the chloroplast fructose-1,6-bisphosphase (FBPase) from wheat (Lloyd et al., 1991), the nuclear photosynthetic ST-LS1 from potato (Stockhaus et al., 1989), and the phenylalanine ammonia-lyase (PAL) and chalcone synthase (CHS) genes from *Arabidopsis thaliana* (Leyva et al., 1995). Also shown to be active in photosynthetically active tissues are the ribulose-1,5-bisphosphate carboxylase (RUBISCO) isolated from eastern larch (*Larix laricina*) (Campbell et al., 1994); the cab gene, encoding the chlorophyll a/b-binding protein of PSII, isolated from pine (cab6; Yamamoto et al., 1994), wheat (Cab-1; Fejes et al., 1990), spinach (CAB-1;

Luebberstedt et al., 1994), and rice (cab1R: Luan et al., 1992); the pyruvate orthophosphate dikinase (PPDK) from maize (Matsuoka et al., 1993); the tobacco Lhcb1*2 gene (Cerdan et al., 1997); the *Arabidopsis thaliana* SUC2 sucrose-H+ symporter gene (Truernit et al., 1995); and the thylacoid membrane proteins, isolated from spinach (psaD, psaF, psae, PC, FNR, atpC, atpD, cab, rbcS; Oelmueller et al., 1992). Other chlorophyll a/b-binding proteins have been studied and described in the literature, such as LhcB and PsbP from white mustard (Sinapis alba; Kretsch et al., 1995). Promoters that cause the production of SBPase specifically in the stems, leaves, or specific cell types in these tissues are useful in the present invention. For example, the RbcS bundle sheath-specific promoter is one such tissue-specific promoter. Thus native promoters for maize, wheat, barley, and rice may be obtained and used in the present invention as well as heterologous promoters from other organisms shown to function in a constitutive/tissue-specific manner. Carbon metabolism in C4 plants such as corn is more specialized than in C3 plants such as tobacco. In C4 plants, metabolites generated by the Calvin cycle in the chloroplast of bundle sheath cells must be transported to the cytoplasm of the mesophyll cells where sucrose biosynthesis takes place. Therefore, cell-specific promoters are needed for correct gene expression in the proper cell type in C4 crops. For example, the RbcS bundle sheath-specific promoter would be useful for expressing SBPase in the appropriate cell type in corn.

For the purpose of expressing an sbpase gene (encoding a light-regulated protein or a protein modified to be constitutively active) only when the plant is photosynthetically active, it is preferred that the promoters utilized in the double-stranded DNA molecules of the present invention have expression in the presence of light only. For this purpose, one may choose from a number of promoters for light regulated genes, including FBPase from wheat (Miles, et al., 1993), pyruvate orthophosphate dikinase from maize (Sheen, 1991), and chloroplast aldolase from rice (Kagaya et al., 1995).

The RNA produced by a DNA construct of the present invention may also contain a 5' non-translated leader sequence. This sequence can be derived from the promoter selected to express the gene and can be specifically modified so as to increase translation of the MRNA. The 5' non-translated regions can also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be derived from an unrelated promoter or coding sequence.

Generally, optimal expression in monocotyledonous and some dicotyledonous plants is obtained when an intron sequence is inserted between the promoter sequence and the structural gene sequence or, optionally, may be inserted in the structural coding sequence to provide an interrupted coding sequence. An example of such an intron sequence is the HSP 70 intron described in WO 93/19189.

Polyadenylation Signal

The 3' non-translated region of the chimeric plant gene contains a polyadenylation signal that functions in plants to cause the addition of polyadenylate nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes like the soybean storage protein genes and the small subunit of the ribulose-1,5-bisphosphate carboxylase (ssRUBISCO) gene.

Plastid-directed Expression of Sedoheptulose 1,7-bisphosphatase Activity

In one embodiment of the invention, the sbpase gene may be fused to a chloroplast transit peptide, in order to target the SBPase protein to the plastid. As used hereinafter, chloroplast and plastid are intended to include the various forms of plastids including amyloplasts. Many plastid-localized proteins are expressed from nuclear genes as precursors and are targeted to the plastid by a chloroplast transit peptide (CTP), which is removed during the import steps. Examples of such chloroplast proteins include the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II, and thioredoxin F. The plastid targeting sequence can be, but is not limited to, the native chloroplast targeting peptide (CTP) identified in the wheat SBPase cDNA. It has been demonstrated that non-plastid proteins may be targeted to the chloroplast by use of protein fusions with a CTP and that a CTP sequence is sufficient to target a protein to the plastid. Those skilled in the art will also recognize that various other chimeric constructs can be made that utilize the functionality of a particular plastid transit peptide to import the enzyme into the plant cell plastid depending on the promoter tissue specificity.

Combinations with Other Transgenes

The effect of sbpase in transgenic plants may be enhanced by combining it with other genes that positively affect carbohydrate assimilation or content, such as a gene encoding for a sucrose phosphorylase as described in PCT Publication WO 96/24679, or ADPGPP genes such as the *E. coli* glgC gene and its mutant glgC16. PCT Publication WO 91/19806 discloses how to incorporate the latter gene into many plant species in order to increase starch or solids. Another gene that can be combined with sbpase to increase carbon assimilation, export or storage is a gene encoding for sucrose phosphate synthase (SPS). PCT Publication WO 92/16631 discloses one such gene and its use in transgenic plants. Another gene with which SBPase can be combined is fructose 1,6-bisphosphate aldolase.

Plant Transformation/Regeneration

In developing the nucleic acid constructs of this invention, the various components of the construct or fragments thereof will normally be inserted into a convenient cloning vector, e.g., a plasmid that is capable of replication in a bacterial host, e.g.,*E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A double-stranded DNA molecule of the present invention containing an sbpase gene can be inserted into the genome of a plant by any suitable method. Preferred methods of transformation of plant cells or tissue are the *Agrobacterium* mediated transformation method and the biolistics or particle-gun mediated transformation method. Suitable plant transformation vectors for the purpose of *Agrobacterium* mediated transformation include those derived from a Ti plasmid of *Agrobacterium tumefaciens,* as well as those disclosed, e.g., by Herrera-Estrella et al. (1983), Bevan (1984), Klee et al. (1985) and EPO publication 120,516. In addition to plant transformation vectors derived from the Ti or root-inducing (Ri) plasmids of *Agrobacterium,* alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of a sbpase gene in monocots using electroporation or particle-gun mediated transformation is composed of the following: a promoter that is constitutive or tissue-specific; an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., 1983). This expression cassette may be assembled on high copy replicons suitable for the production of large quantities of DNA.

An example of a useful Ti plasmid cassette vector for plant transformation is pMON17227. This vector is described in PCT Publication WO 92/04449 and contains a gene encoding an enzyme conferring glyphosate resistance (denominated CP4), which is an excellent selection marker gene for many plants. The gene is fused to the *Arabidopsis* EPSPS chloroplast transit peptide (CTP2) and expressed from the FMV promoter as described therein. When adequate numbers of cells (or protoplasts) containing the sedoheptulose-1,7-bisphosphatase gene or cDNA are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al. (1984); Shimamoto et al. (1989); Fromm (1990); Vasil et al. (1990); Vasil et al. (1992); Hayashimoto (1990); and Datta et al. (1990).

Plants that can be made to have enhanced and/or improved carbon assimilation, increased carbon export and partitioning by practice of the present invention include, but are not limited to, Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The following examples are provided to better elucidate the practice of the present invention and should not be interpreted in any was to limit the scope of the present invention. Those skilled in the art will recognize that various modifications, truncations, etc., can be made to the methods and genes described herein while not departing from the spirit and scope of the present invention.

EXAMPLES

Example 1 cDNA Cloning and Overexpression of SBPase for Antibody Production

To isolate the region of the gene encoding the mature SBPase protein (no CTP), an RT-PCR reaction was performed. One microgram of *Triticum aestivum,* CV OSLO leaf RNA was combined with 100 pmol of random hexamer primers (BRULife Technologies Inc, Gaithersburg, Md.) or with 100 pmol of oligo dT primer (Promega, Madison, Wis.), heated for 5 minutes at 75° C., and chilled on ice. First strand cDNA synthesis was performed using Superscript II™ reverse transcriptase (BRL/Life Technologies Inc, Gaithersburg, Md.) according to the manufacturer's protocol. The terminated reverse transcription reaction was diluted 1:7. Three microliters of the diluted first strand synthesis products were combined with 100 μM of each dNTP, 50 pmol of a gene specific primer with homology to the 5' end of the gene designed to generate an NdeI cleavage site for subcloning purposes (5'-ACATATGTGCGC-GATCGGCGA-3', SEQ ID NO:1), 50 pmol of a gene specific primer with homology to the 3' end of the gene (5'-GGATCCAGAAGATTATAGGCG-3', SEQ ID NO:2), and 5 Units of PWO™ polymerase (Boehringer, Mannheim, Germany) in 100 μL. PCR cycling conditions were as follows: 95° C., 40 seconds; 56° C., 1 minute; 72° C., 1 minute 30 seconds (5 cycles) followed by 95° C., 40 seconds; 61° C., 1 minute; 72° C., 1 minute 30 seconds (30 cycles). The 982 bp SBPase mature protein gene PCR product was gel purified, cloned into the PCR-Blunt cloning vector (Invitrogen, Carlsbad, Calif.) to form pMON47205 (FIG. 1), and transformed into competent *E. coli* cells. Clones bearing inserts were selected on media containing kanamycin, plasmid purified, and digested with BamHI to select for the proper orientation in the cloning vector. Sequence analysis revealed that predicted amino acid sequence (SEQ ID NO:9) is identical to the published sequence (Raines et al., 1992) starting at residue 73, although the nucleotide sequence (SEQ ID NO:3) differs at 2 positions (residue 294 from T to C; residue 572 from C to T). The selected plasmids were restricted with NdeI and BamHI, directionally cloned under the control of the IPTG inducible T7 polymerase promoter of pET 15b bacterial expression vector (Novagen, Madison, Wis.) linearized with NdeI/BamHI, and transformed into DH5α. Transformants were screened by NdeI/BamHI restriction analysis and clones possessing an insert were selected, plasmid purified, and transformed into *E. coli* BL21(DE3) for protein expression purposes.

*E. coli* BL21(DE3) cells transformed with the pETl15b-SBPase cDNA construct were induced with 2 mM IPTG for 2.5 hours after which a distinct protein band of about 38 kDa was apparent on an SDS-PAGE gel, which correlates with the size of the subunit polypeptide chain of the dimeric SBPase. Protein expressed by the mature SBPase was purified based on the affinity of histidine residues for immobilized nickel ions. The purification was performed under denaturing conditions using Ni- NTA Superflow resin (QIAGEN, Valencia, Calif.) as described in the manufacturer's protocol. A 2 mL fraction containing 1 mg of purified SBPase protein emulsified with an equal volume of Complete Adjuvant (Sigma, St. Louis, Mo.) was used to inoculate a goat for antibody production using standard methods (Antech Company, St. Louis, Mo.). The preimmune serum showed no reactivity with SBPase.

Example 2 cDNA Cloning of SBPase for Expression in Plants

Figure 2:
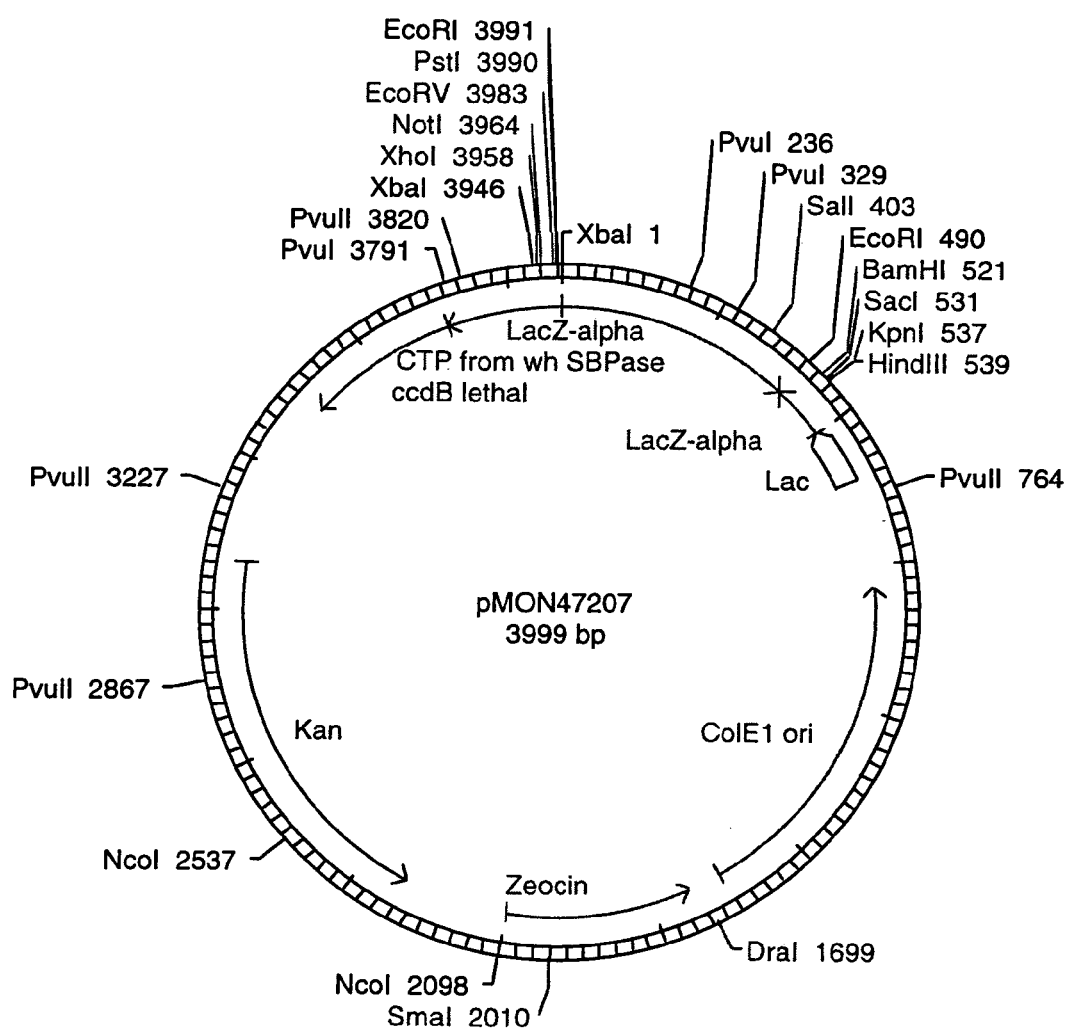
FIG. 2 shows a plasmid map for cloning vector pMON47207.

To clone the region of the SBPase gene encoding the chloroplast transit peptide, a modified anchored PCR procedure for the rapid amplification of cDNA ends (Frohman, 1990; Jain et al., 1992) was used. Eight hundred nanograms of total RNA was combined with 10 ng of a gene-specific primer (5'-TTCCTCAGAGCACGCGTACTTG-3', SEQ ID NO:4),heated to 75° C. for 5 minutes, and chilled on ice. First strand DNA synthesis was performed using Superscript II™ reverse ranscriptase (BRL/Life Technologies Inc, Gaithersburg, Md.) according to the supplier's protocol. The terminated reverse transcription reaction was treated with one unit of ribonuclease H for 20 minutes at 37° C., 5 minutes at 95° C., and chilled on ice. Excess primers and dNTPs were removed by centrifugation at 2,000×g through an Ultrafree-MC filterfuge (30,000 MW cutoff, Millipore, Bedford, Mass.), and the retentate was concentrated to 15 μL on a Savant Speedvac (Savant Instruments, Holbrook, N.Y.). The first-strand synthesis products were combined with 10 μL of tailing mix (1× tailing buffer [BRL/Life Technologies Inc, Gaithersburg, Md.], 0.4 mM dATP, 10 units of terminal deoxytransferase) and incubated at 37° C. for 10 minutes. The reaction mixture was heated to 95° C. for 5 minutes, diluted to 0.5 mL with TE, pH 8.0, and utilized as a cDNA pool. A mixture of 10 μL of the cDNA pool, 10 μL PWO™ polymerase 10× buffer (BRL/Life Technologies Inc, Gaithersburg, Md.), 100 μM of each dNTP, 25 pmol of a gene specific primer (SEQ ID NO:4), 10 pmol of the poly(dT) adaptor primer (5'-GGGTCGACATTCTAGACAGAAT-TCGTGGACC(T)$_{21}$-3'; SEQ ID NO:5), and 5 units of PWO™ polymerase (BRL/Life Technologies Inc, Gaithersburg, Md.) in 100 μL was amplified. PCR cycling conditions were as follows: 95° C., 2 minutes; 45° C., 5 minutes; 72° C., 40 minutes (1 cycle) followed by 95° C., 50 seconds; 48° C., 1 minute; 72° C., 1 minute (3 cycles). The PCR products were purified away from the excess primers by ethanol precipitation. The pellet was resuspended in 50 μL of water and subjected to another round of amplification using a new nested gene specific primer (5'-CATGGGAGTACTC-CAACGCCTC-3', SEQ ID NO:6) and an adaptor primer (5'-GGGTCGACATTCTAGACAGAA-3', SEQ ID NO:7). PCR cycling conditions were as follows: 95° C., 40 seconds; 58° C., 1 minute; 72° C, 30 seconds (30 cycles). The ~500 bp PCR product was gel purified, subcloned into the PCR-Blunt cloning vector (Invitrogen, Carlsbad, Calif.) to form pMON47207 (FIG. 2), and transformed into One Shot Top 10 Cells (Invitrogen, Carlsbad, Calif.) for further characterization. Sequence analysis (SEQ ID NO:8) showed that this sequence differs from the published sequence in 9 positions (30, C to T; 42, G to C; 44, A to G; 187, C to A; 204, C to G; 228, C to G; 259, C to T; 348, G to C; and 351, C to G) resulting in three predicted amino acid changes (30, Arg to Cys; 44, His to Arg; 207, Gln to Glu).

Figure 3:
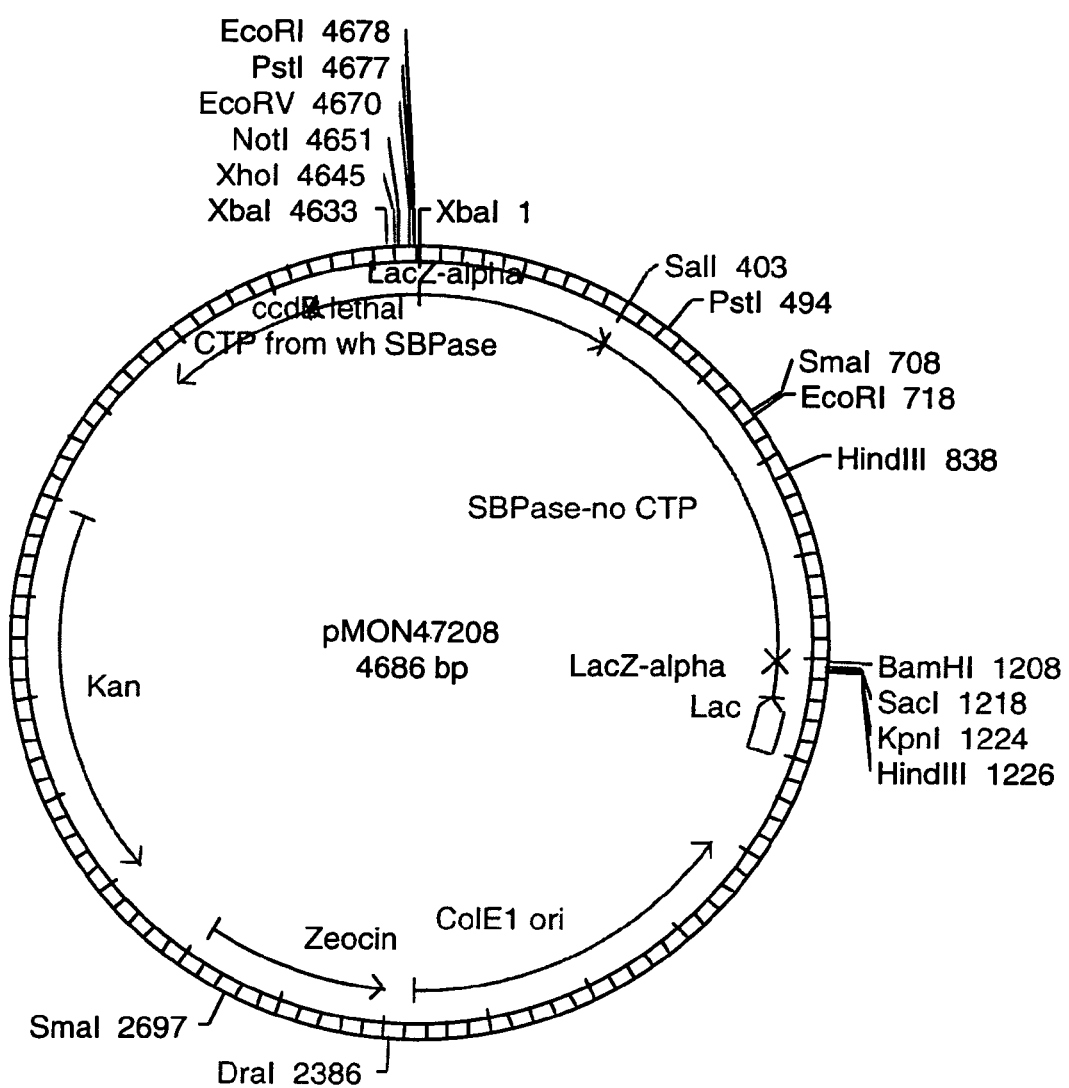
FIG. 3 shows a plasmid map for cloning vector pMON47208.
Figure 4:
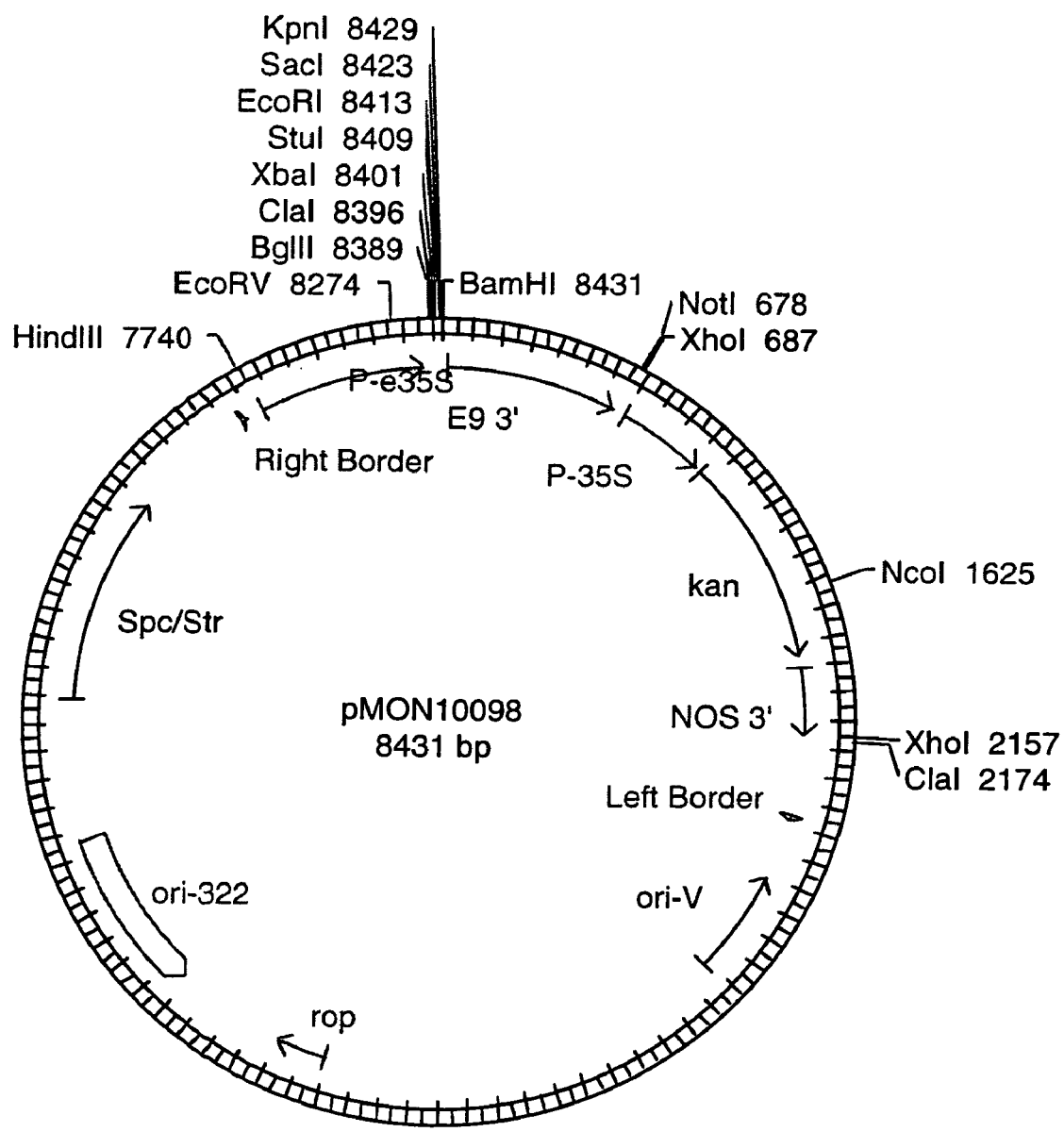
FIG. 4 shows a plasmid map for plant transformation vector pMON10098.
Figure 5:
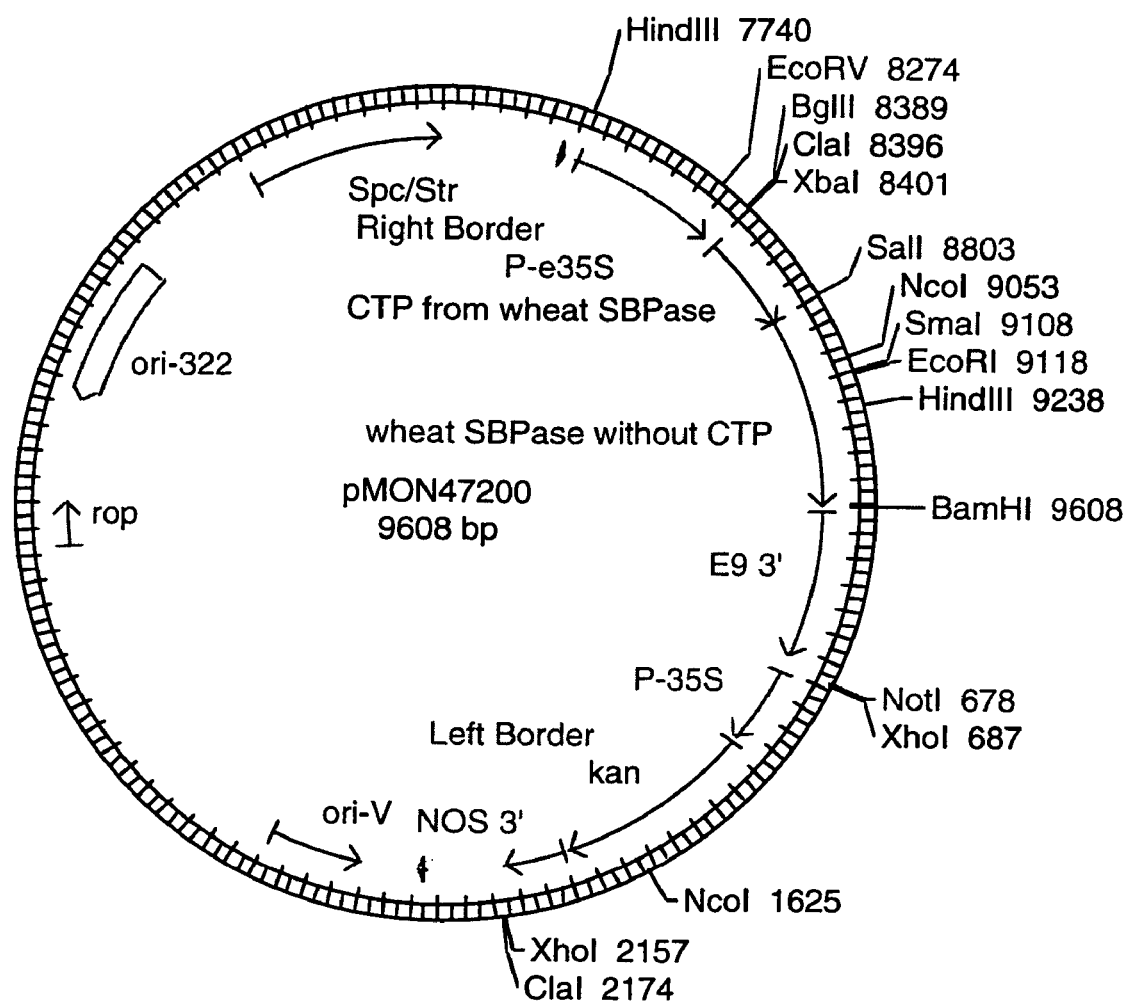
FIG. 5 shows a plasmid map for plant transformation vector pMON47200.

In order to test the expression of the wheat SBPase in plants, pMON47205 (FIG. 1) and pMON47207 (FIG. 2) were each restricted with SalI and BamHI. The fragments containing sequence encoding the mature SBPase and the CTP region, respectively, were gel purified, and ligated together to form pMON47208 (FIG. 3). pMON47208 was restricted with XbaI and BamHI and the sequence encoding SBPase was gel purified and ligated to XbaI/BamHI— linearized pMON10098 (FIG. 4). The final vector formed was pMON47200 (FIG. 5) with the CaMV E35S promoter, the coding sequence of the entire SBPase gene, the NOS 3'-untranslated polyadenylation region, and kanamycin resistance for selection in plants.

Example 3

Transient Expression of Maize Protoplasts

Figure 6:
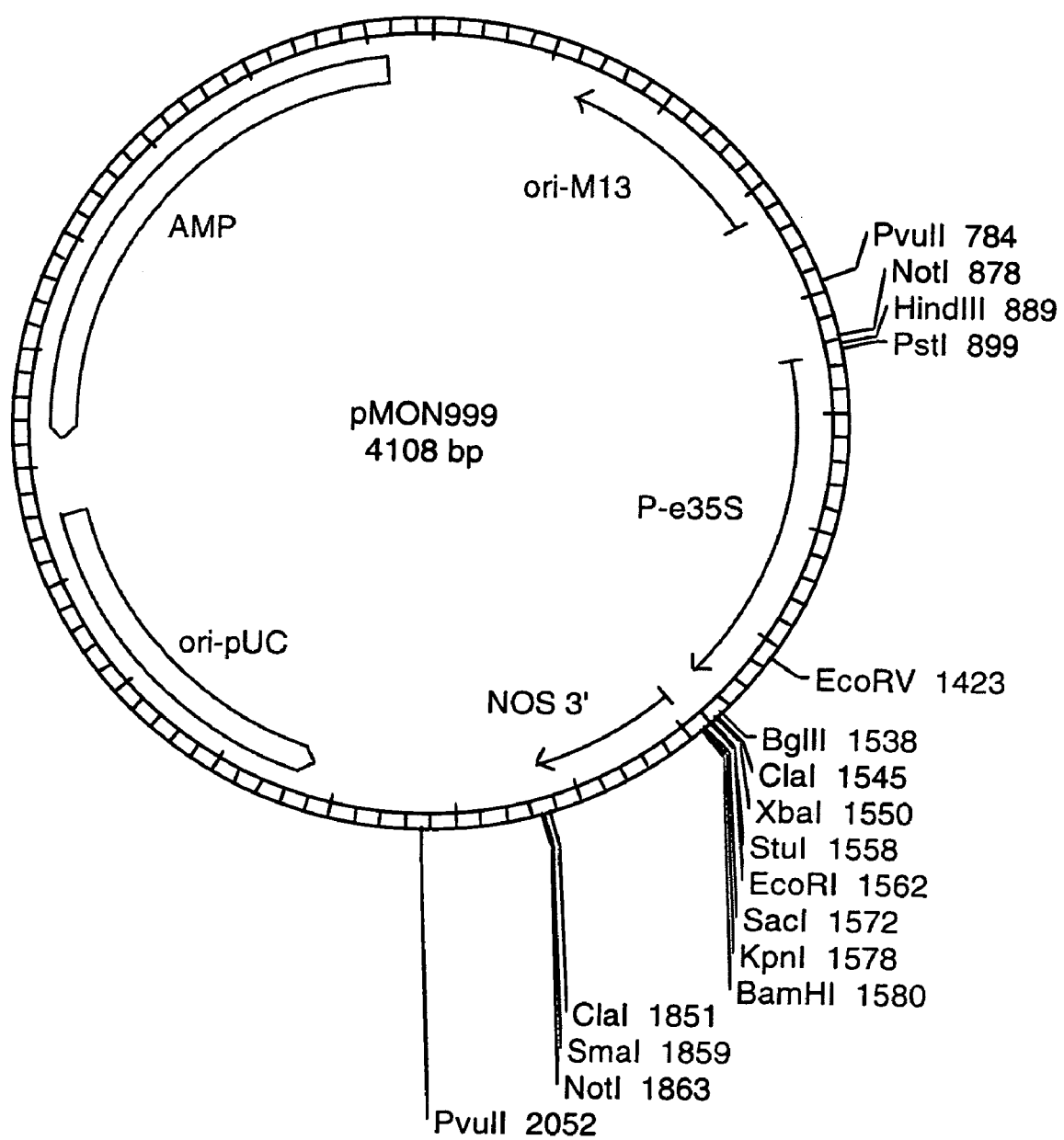
FIG. 6 shows a plasmid map for shuttle vector pMON999.
Figure 7:
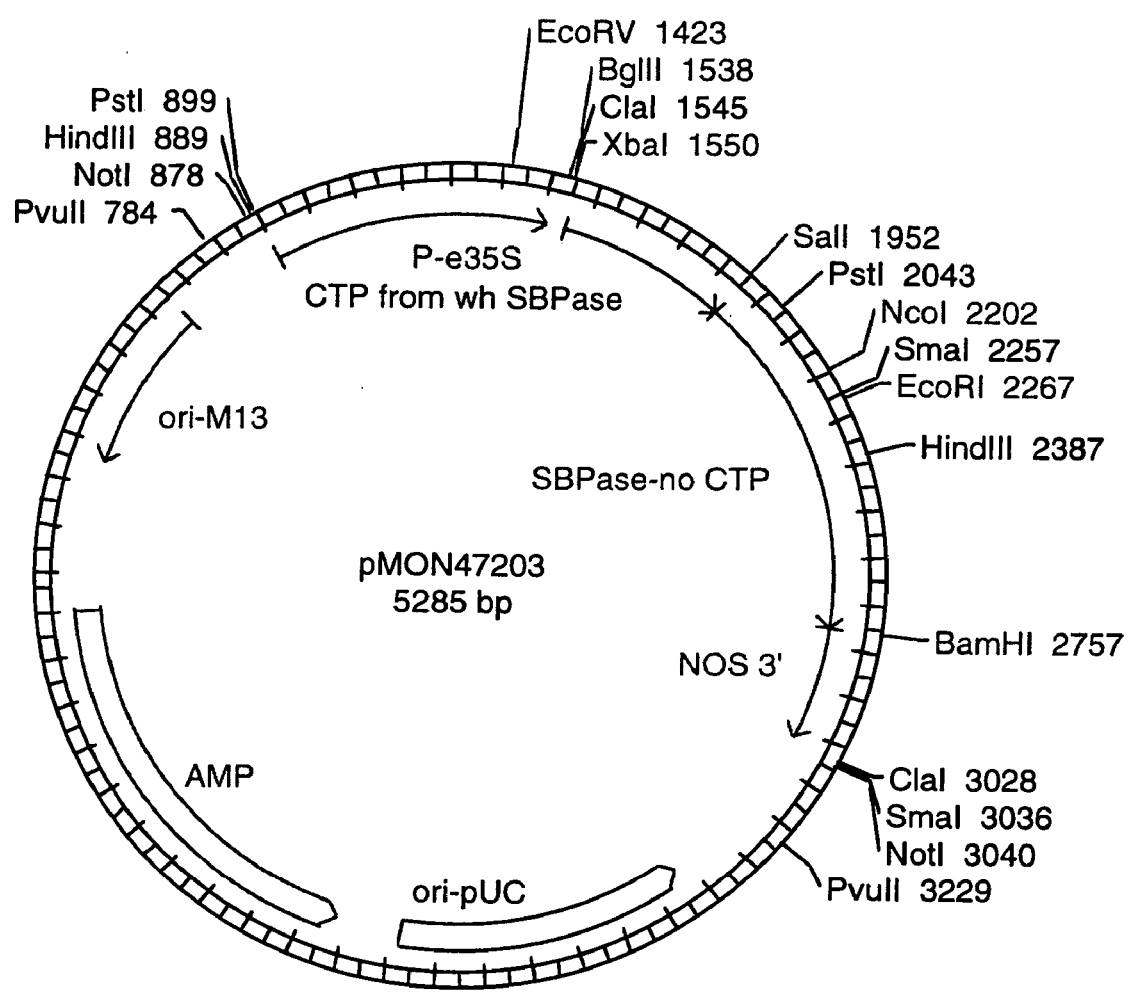
FIG. 7 shows a plasmid map for transient transformation vector pMON47203.

In order to test the expression of the wheat SBPase subunits and their assembly into active enzymes, vectors were constructed to contain the CaMV E35S promoter, the coding sequence for the entire SBPase protein including the CTP, the NOS 3' termination signal, and ampicillin resistance for selection in E. coli. The SBPase gene was isolated as an XbaI-BamHI fragment from pMON47200. The SBPase gene was ligated into the XbaI-BamHI CaMV E35S, NOS 3' bearing region of pMON999 (FIG. 6) to give pMON47203 (FIG. 7). The DNA constructs were electroporated into maize protoplasts according to the method of Sheen et al. (1991).

Example 4

Analysis of Transformed Maize Protoplasts

Pelleted protoplast samples transformed with pMON47203 (SBPase) and no DNA were thawed in 0.18 mL of extraction buffer (50 mM HEPES pH 7.5, 1 mM fructose bisphosphate, 1 mM sedoheptulose-1,7-bisphosphate, 10 mM $MgCl_2$, 10 mM $MnCl_2$, 10 mM DTT, 1% polyvinylpolypyrrolidone, 10% glycerol, and Complete™ Protease Inhibitors (Boehringer, Mannheim, Germany)) on ice. The cells in each suspension were vortexed well and clarified at 2,000×g for 15 minutes. The supernatants were desalted using G25 spin columns (The Nest Group, Southboro, Mass.). Total protein content of the desalted protein was determined using the BioRad microprotein assay (Bio-Rad, Hercules, Calif.) according to the manufacturer's protocol.

Protein expression and size were determined by Western blot analysis (FIG. 8). Significantly more protein was detected by cross-reactivity with goat anti-wheat SBPase antibodies in protoplasts transformed with pMON47203 than control protoplasts, indicating successful over-expression of SBPase enzyme in plant cells. The mobility of the wheat SBPase (pMON47203) expressed in corn protoplasts was approximately 38 kDa, the same as the endogenous wheat leaf SBPase, indicating correct processing of the CTP.

SBPase activity was assayed by allowing hydrolysis of SBP for 10 minutes followed by measurement of phosphate liberation. The reaction was initiated by combining 20 μL of buffer (100 mM Tris, 8.2, 10 mM $MgCl_2$, 10 mM DTT, 1.5 mM EDTA, 10% glycerol) containing 5 μg of desalted protein extract with 55 μL of assay buffer (50 mM Tris, 8.2, 10 mM $MgCl_2$, 10 mM DTT, 1.5 mM EDTA, 0.27 mM sedoheptulose-1,7-bisphosphate). The reaction was stopped after a 10 minute incubation at room temperature by adding 30 μL of 1 M perchloric acid. The precipitated protein was removed by centrifugation, 250 μL of developer (1% ammonium molybdate, 1N HCl, 0.05% Malachite green (Itaya and Michio, 1966)) was added to 50 μL of supernatant, and the amount of phosphate liberated was determined by measuring absorbance at 660 nm. A phosphate standard curve (0.5–10 nmol) was utilized for quantitation. Protoplasts transformed with pMON47203 liberated 3-fold more phosphate from sedoheptulose-1,7-bisphosphate than control protoplasts (FIG. 9).

The high level of activity observed for the protoplasts transformed with wheat SBPase gene provides evidence that the SBPase protein detected by Western blot analysis is functional.

Example 5

Wheat SBPase Expression in Tobacco

In order to test the effects of over-expressing SBPase from wheat in tobacco, pMON47200 (FIG. 5) was prepared and used as the transformation vector for tobacco plant transformation. Tobacco plant cells were transformed by Agrobacterium mediated transformation according to Horsch et al. (1985). The plant transformation vectors were mobilized into the ABI Agrobacterium strain by electroporation.

Growth chamber-grown tobacco transformant lines were generated and first screened by Western blot analysis to identify expressors using goat antibody raised against wheat-expressed SBPase. It was not, however, possible to separate the endogenous tobacco SBPase from the transgenic wheat SBPase using gradient SDS-PAGE gels or isoelectric focusing gels for these tobacco transformant lines.

EXAMPLE 6 cDNA Cloning of SBPase from *Chlorella sorokiniana* for Expression in Plants

To determine the sequence of the gene encoding SBPase protein from *Chlorella sorokiniana*, several RT-PCR reactions were performed. One microgram of *Chlorella sorokiniana* RNA was combined with 100 pmol of oligo dT primer (Promega, Madison, Wis.), heated for 5 minutes at 75° C., and chilled on ice. First strand CDNA synthesis was performed using Superscript II™ reverse transcriptase (BRL/Life Technologies Inc, Gaithersburg, Md.) according to the manufacturer's protocol. The terminated reverse transcription reaction was diluted 1:7. Twenty microliters of the diluted first strand synthesis products were combined with 100 μM of each dNTP, 50 pmol of a degenerate primer with homology to the 5' end of the gene (5'-GGIACIATHTYG-GIGTITGG -3', SEQ ID NO: 10), 50 pmol of a gene specific primer with homology to the 3' end of the gene (5'-RTA-ICKIARIGTRTAYTTYTC -3', SEQ ID NO:11), and 5 Units of Taq polymerase (BRL/Life Technologies Inc, Gaithersburg, Md.) in 100 μL. PCR cycling conditions were as follows: 95° C., 5 minutes (1 cycle) followed by 95° C., 40 seconds; 35° C., 1 minute; 72° C., 1 minute (5 cycles) followed by 95° C., 40 seconds; 40° C., 1 minute; 72° C., 1 minute (30 cycles). The 550 bp PCR product that was 250 bp larger than the expected size was gel purified, cloned into the PCR-Blunt cloning vector (Invitrogen, Carlsbad, Calif.), and transformed into competent *E. coli* cells. Plasmid was purified from clones containing insert that had been selected on media containing kanamycin. Sequence analysis revealed that the predicted amino acid sequence of this 550 bp PCR product is 41% identical to the *Chlamydomonas reinhardtii* sequence. Residues 226–251 of the *Chlamydomonas reinhardtii* sequence was 81% identical to the *Chlorella* sequence and residues 252–287 of the *Chlamydomonas* sequence was 86% identical but there was a gap encoding 62 *Chlorella*, residues presumably corresponding to an intron. Therefore this fragment was most likely amplified from contaminating genomic DNA. The 297 bp of coding sequence was used to design primers for 5' RACE and 3' RACE to identify the sequence of the rest of the gene.

To clone the remaining 5' sequence of the SBPase, a modified anchored PCR procedure for the rapid amplification of cDNA ends (Frohman, 1990; Jain et al., 1992) was used. Nine hundred nanograms of total *Chlorella sorokiniana* RNA was combined with 20 pmol of a gene-specific primer (5'-GATGGTCTCGGCTCTCCTTCACG-3', SEQ ID NO:13), heated to 75° C. for 5 minutes, and chilled on ice. First strand DNA synthesis was performed using Thermoscrip™ reverse transcriptase (BRL/Life Technologies Inc, Gaithersburg, Md.) at 55° C. according to the supplier's protocol. The terminated reverse transcription reaction was treated with one unit of ribonuclease H for 20 minutes at 37° C., 5 minutes at 95° C., and chilled on ice. Excess primers and dNTPs were removed by centrifugation at 2,000×g through an Ultrafree-MC filterfuge (30,000 MW cutoff, Millipore, Bedford, Mass.), and the retentate was concentrated to 15 μL on a Savant.Speedvac (Savant Instruments, Holbrook, N.Y.). The firststrand synthesis products were combined with 10 μL of tailing mix (1× tailing buffer [BRL/Life Technologies Inc, Gaithersburg, Md.], 0.4 mM dATP, 10 units of terminal deoxytransferase) and incubated at 37° C. for 10 minutes. The reaction mixture was heated to 95° C. for 5 minutes, diluted to 0.2 mL with 10 mM Tris, pH 8.5, and utilized as a cDNA pool. A mixture of 20 μL of the cDNA pool, 10 μL PWO™ polymerase 10× buffer (BRL/life Technologies Inc, Gaithersburg, Md.), 100 μM of each dNTP, 25 pmol of a gene specific primer (SEQ ID NO:13), 10 pmol of the poly(dT) adaptor primer (5'-CCCTCGACAT-TCTAGACAGAATTCGTGGATCC(T)$_{21}$-3'; SEQ ID NO:5), and 5 units of PWO™ polymerase (BRL/Life Technologies Inc, Gaithersburg, Md.) in 100 μL was amplified. PCR cycling conditions were as follows: 95° C., 2 minutes; 45° C., 5 minutes; 72° C., 40 minutes (1 cycle) followed by 95° C., 50 seconds; 48° C., 1 minute; 72° C., 1 minute (3 cycles). The PCR products were purified away from the excess primers by ethanol precipitation. The pellet was resuspended in 50 μL of water and combined with 10 μl of PWO™ polymerase 10× buffer (BRL/Life Technologies Inc, Gaithersburg, Md.) in 100 μl 50 μM of each dNTP, 50 pmol a new nested gene specific primer (5'-CAGCCACTGC-CATCGTC-3', SEQ ID NO:14), 50 pmol of an adaptor primer (5'-GGGTCGACATTCTAGACAGAA-3', SEQ ID NO:7), 5 Units of PWO™ polymerase (BRL/Life Technologies Inc, Gaithersburg, Md.). PCR cycling conditions were as follows: 95° C., 40 seconds; 48° C., 1 minute; 72° C., 1 minute, 30 seconds (30 cycles). The 400 bp PCR product was gel purified, subcloned into the PCR-Blunt TOPO II cloning vector (Invitrogen, Carlsbad, Calif.) and transformed into competent *E. coli* cells for further characterization. Sequence analysis showed that this PCR fragment was part of the 5' sequence of the *Chlorella sorokiniana* SBPase.

This sequence was then used to design additional primers to clone the remaining 5' sequence of the SBPase using the modified anchored PCR procedure for the rapid amplification of cDNA ends (Frohman, 1990; Jain et al., 1992). Nine hundred nanograms of total RNA was combined with 20 pmol of a gene-specific primer (5'-GATGGTCTCGGTCTC-CTTCACG-3', SEQ ID NO:15), heated to 75° C. for 5 minutes, and chilled on ice. First strand DNA synthesis was performed using Thermoscript™ reverse transcriptase (BRL/Life Technologies Inc, Gaithersburg, Md.) at 55° C. according to the supplier's protocol. The terminated reverse transcription reaction was treated with one unit of ribonuclease H for 20 minutes at 37° C., 5 minutes at 95° C., and chilled on ice. Excess primers and dNTPs were removed by centrifugation at 2,000×g through an Ultrafree-MC filterfuge (30,000 MW cutoff, Millipore, Bedford, Mass.), and the retentate was concentrated to 15 µL on a Savant Speed-vac (Savant Instruments, Holbrook, N.Y.). The first-strand synthesis products were combined with 10 µL of tailing mix (1× tailing buffer [BRL/Life Technologies Inc, Gaithersburg, Md.], 0.4 mM dATP, 10 units of terminal deoxytransferase) and incubated at 37° C. for 10 minutes. The reaction mixture was heated to 95° C. for 5 minutes, diluted to 0.2 mL with TE, pH 8.0, and utilized as a cDNA pool. A mixture of 20 µof the cDNA pool, 10 µL HotStarTaq™ polymerase 10× buffer (Qiagen, Valencia, Calif.), 20 µl of Q 5× buffer (Qiagen, Valencia, Calif.) 50 µM of each dNTP, 25 pmol of a gene specific primer (5'-TCCTCAGAGCACGCCAGCT-TGC-3', SEQ ID NO:16), 10 pmol of the poly(dT) adaptor primer (5'-GGGCGACATTCTAGACAGAATTCGTG-GATCC(T)$_{21}$-3'; SEQ ID NO:5), and 5 units of HotStar-Taq™ polymerase (Qiagen, Valencia, Calif.) in 100 µL was amplified. PCR cycling conditions were as follows: 95° C., 15 minutes; 45° C., 5 minutes; 72° C., 40 minutes (1 cycle) followed by 95° C., 50 seconds; 48° C., 1 minute; 72° C., 1 minute (3 cycles). The PCR products were purified away from the excess primers by ethanol precipitation. The pellet was resuspended in 50 µL of water and combined with 10 µL HotStarTaq™ polymerase 10× buffer (Qiagen, Valencia, Calif.), 20 µl of Q 5× buffer (Qiagen, Valencia, Calif.), 50 µM of each dNTP 50 pmol of new nested gene specific primer (5'-AGCTGCTCATCGCCGAACGAGTG-3', SEQ ID NO:17), 50 pmol of an adaptor primer (5'-GGGTCGA-CATTCTAGACAGAA-3', SEQ ID NO:7), and 5 Units of HotStarTaq™ polymerase (Qiagen, Valencia, Calif.). PCR cycling conditions were as follows: 95° C., 15 minutes (1 cycle) followed by 95° C., 40 seconds; 50° C., 1 minute; 72° C., 1 minute, 30 seconds (30 cycles). The 380 bp PCR product was gel purified, subcloned into the PCR-Blunt TOPO II cloning vector (Invitrogen, Carlsbad, Calif.) and transformed into competent E. coli cells for further characterization. Sequence analysis showed that this PCR fragment contains the remaining 5' sequence of the Chlorella SBPase.

PCR was used to isolate the remaining 3' sequence of the SBPase from a Chlorella sorokiniana cDNA library in pSportl constructed using Superscript™ Plasmid System for cDNA Synthesis and Plasmid Cloning (BRL/Life Technologies Inc, Gaithersburg, Md.) according to the supplier's protocols. One microgram of Chlorella sorokiniana RNA was combined with 100 pmol of oligo dT primer (Promega, Madison, Wis.), heated for 5 minutes at 75° C., and chilled on ice. First strand cDNA synthesis was performed using Thermoscript™ reverse transcriptase (BRL/Life Technologies Inc, Gaithersburg, Md.) at 60° C. according to the manufacturer's protocol instead of the Superscript™ reverse transcriptase (BRL/Life Technologies Inc, Gaithersburg, Md.) provided with the kit. A mixture of 200 ng of library DNA, 10 µL HotStarTaq™ polymerase 10× buffer (Qiagen, Valencia, Calif.), 50 µM of each DNTP, 50 pmol of a gene specific primer (5'-AGCCTGCTGCAGGACGATGG-3'; SEQ ID NO:18), 50 pmol of the vector specific primer (5'-CCCAGTCACGACGTTGTAAAACG -3'; SEQ ID NO:19), and 5 units of HotStarTaq™ polymerase (Qiagen, Valencia, Calif.) in 100 µL was amplified. PCR cycling conditions were as follows: 95° C., 15 minutes (1 cycle) followed by 95° C., 40 seconds; 62° C., 1 minute; 72° C., 1 minute, 30 seconds (30 cycles). The overlapping 5' and 3' sequences were assembled to give the full length Chlorella sorokiniana SBPase sequence (SEQ ID NO:20) with predicted amino acid sequence (SEQ ID NO:12).

TABLE 1

Comparison of Chlorella sorokiniana SBPase derived amino acid sequence (SEQ ID NO:12) with known SBPase amino acid sequences. The alignments were made using the Bestfit program to determine percentage homology in the table below. BestFit program uses the local homology algorithm of Smith and Waterman (1981) to find the best segment of similarity between two sequences.

|  | Similarity | Identity |
| --- | --- | --- |
| Arabidopsis thaliana | 76.7% | 71.6% |
| Chlamydomonas reinhardtii | 82.0% | 78.0% |
| Spinacia oleracea | 74.3% | 68.4% |
| Triticum aestivum | 72.0% | 66.8% |

Example 7

Cloning Genes Encoding Dual FBPase and SBPase Activity

Bisphosphatase genes from the facultative chemoautotroph Ralstonia eutropha (Alcaligenes eutrophus) and from the algae Synechococcus lepoliensis encode proteins with a dual activity, FBPase and SBPase, in the Calvin cycle (Yoo and Bowien, 1995; Gerbling et al., 1986). A gene encoding a protein with SBPase activity will be cloned from Ralstonia eutropha using PCR based on the sequence described in Yoo and Bowien (1995). This gene will then be fused to a chloroplast transit peptide, in order to target the SBPase protein to the plastid.

Example 8

Chlorella and Ralstonia SBPase Expression in Tobacco

In order to test the effects of over-expressing wild type or deregulated Chlorella as well as Ralstonia SBPase in tobacco, each gene will first be cloned into the pCR®-Blunt II™ cloning vector (Invitrogen, Carlsbad, Calif.). Each vector will then be digested with EcoRI and the gel purified fragments encoding each of the SBPases will be ligated individually to EcoRI-linerarized pMON10098 (FIG. 4). Each of the 3 vectors will be used for tobacco plant transformation, as described in Horsch et al. (1985). The plant transformation vectors are mobilized into the ABI Agrobacterium strain by electroporation.

Growth chamber-grown tobacco transformant lines are generated and first screened by Western blot analysis to identify expressors using goat antibody raised against wheat-expressed SBPase. Subsequently, for wild type Chlorella-SBPase, deregulated Chlorella SBPase- and Ralstonia SBPase-expressing tobacco lines, leaf samples taken at various stages of plant development will be analyzed for diurnal changes in leaf nonstructural carbohydrates (sucrose, glucose, and hydrolyzed starch into glucose) by means of the Sucrose/D-Glucose/D-Fructose kit (Boehringer Mannheim, Germany).

Thirty to fifty milligrams of frozen tobacco leaf tissue samples will be incubated in 1 mL of 85° C. water for 15 minutes. Tubes will be centrifuged for 1 minute at 10,000×g and the supernatants saved for soluble sugar analysis. The pellet will be resuspended in 1 mL of 85° C. water, mixed with a Vortex, and centrifuged as described above. The supernatant will be carefully removed and added to the previous supernatant fraction for soluble sugar (sucrose and glucose) analysis by the Sucrose/D-Glucose/D-Fructose kit (Boehringer Mannheim, Germany).

The starch will be extracted from the pellet using by adding 3 mL of 0.1 M sodium acetate, pH 5.6 to the pellet and incubating at 90° C. for 10 minutes. Once cool, 3 mL of 1% amyloglucosidase in 0.1 M sodium acetate, pH 5.6 will be added and vortexed. The samples will be incubated in a water bath at 50° C. for 3 hours, vortexing every half hour. After centrifugation in a table top centrifuge at 900×g for 30 minutes, the supernatants will be analyzed for glucose content. The free glucose will be adjusted to anhydrous glucose (as it occurs in starch by multiplying by the ratio 162/182).

Alteration of carbon assimilation in the transgene plant tissue can be monitored by metabolic profiling using standard HPLC, mass spectroscopy, and enzymatic based metabolite assays.

Example 9

Deregulation of SBPase

In the dark, wheat SBPase is inactive due to disulfide bond formation between Cys-52 and Cys-57 (numbers correspond to mature wheat SBPase, CA Raines et al. 1999. *J. Exp. Bot.* 50: 1–8). In the light, thioredoxin reduces the disulfide linkage resulting in an active enzyme. Modifying the Cys residues through mutagenesis would prevent formation of the disulfide bond and therefore prevent inactivation of the protein by oxidation. Site-directed mutagenesis to change Cys-110 and Cys-115 (numbers correspond to *Chlorella* SBPase including the CTP, SEQ ID NO: 12) to Ser will be performed using the QuikChange™ Site-Direced Mutagenesis Kit (Stratagene, La Jolla, Calif.) using a mutagenic primer (5'-AAGGTGCGCACCGCCTCGTCC-GGCGGCACCGCCTCCGTCAACTCGTTCGGCGA-TG-3'; SEQ ID NO:21) according to the manufacturer's protocol. The resulting sequence SEQ ID NO:22 will be inserted into the appropriate transformation vector and will be used to transform tobacco and corn. The resulting plants will be tested for expression of the SBPase in the plant tissues and enzymatic assays will be run to confirm activity. The plants will be analyzed to determine the improved assimilation of carbon in the plant and its export and storage to sink tissues. The predicted amino acid sequence resulted from the DNA sequence (SEQ ID NO:22) is shown as SEQ ID NO:23.

It should also be understood that the examples and embodiments described herein are for illustrative purposes only and that various modifications or changes in light thereof will be suggested to persons skilled in the art and are to be included within the spirit and purview of this application and the scope of the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

REFERENCES CITED

Ammirato et al. (1984) *Handbook of Plant Cell Culture—Crop Species.* Macmillan Publ. Co.

Bevan (1984) *Nucleic Acids Res.* 12 (22): 8711–8721.
Cadet and Meunier (1988a) *Biochem. J.* 253: 243–248.
Cadet and Meunier (1988b) *Biochem. J.* 253: 249–254.
Cadet and Meunier (1988c) *Biochem J.* 241: 71–74.
Campbell et al. (1994) *Canadian Journal of Forest Research* 24 (8):1689–1693.
Cerdan et al. (1997) *Plant Molecular Biology* 33 (2): p 245–255.
Datta et al. (1990) *Bio-technology* 8:736–740.
Edwards et al. (1990). *Proc Natl Acad Sci USA* 87 (9): p 3459–3463.
Fejes et al. (1990). *Plant Mol Biol* 15 (6): p 921–932.
Fraley et al. (1983) *Proc Natl Acad Sci USA* 80: 4803–4807.
Frohman (1990) In Gelford, D H, Snincky, J J, White, T J, eds, *PCR Protocols,* Academic Press, San Diego, Calif., pp 28–38.
Fromm, M., (1990) UCLA Symposium on Molecular Strategies for Crop Improvement, Apr. 16–22, 1990. Keystone, Colo.
Gerbling et al. (1986) *Plant Physiol.* 80: 716–720.
Harrison et al. (1998) *Planta* 204: 27–36.
Hayashimoto et al. (1990) *Plant Physiol.* 93:857–863.
Herrera-Estrella et al. (1983) *Nature* 303:209.
Horsch et al. (1985) *Science* 227:1229–1231.
Itaya and Michio (1966) *Clin. Chim. Acta.* 14: 361–366.
Jain et al. (1992) *Biotechniques* 12: 58–59.
Klee et al. (1985) *Bio-Technology* 3(7): 637–642.
Kretsch et al. (1995) *Plant Journal* 7 (5): p 715–729.
Leyva et al. (1995) *Plant Physiology* 108(1):39–46.
Lloyd et al. (1991). *Mol. Gen. Genet.* 225 (2):209–216.
Luan et al. (1992). *Plant Cell* 4 (8):971–981.
Luebberstedt et al. (1994) *Plant Physiology* 104 (3):997–1006.
Maniatis et al. (1982) *Molecular Cloning: A laboratory manual* . Cold Spring Harbor Laboratory Press, Cold Spring Harbor, N.Y.
Martin et al., Plant Mol. Biol. 32 (3), 485–491 (1996)
Matsuoka et al. (1993). *Proc. Natl. Acad. Sci. U.S.A.* 90(20): 9586–9590.
Nishizawa and Buchanan (1981) *J Biol Chem,* 256:6119–6126.
Oelmueller et al. (1992). *Res. Photosynth., Proc. Int. Congr. Photosynth., 9th, Volume* 3: p 219–24. Editor(s): Murata, Norio. Publisher: Kluwer, Dordrecht, Neth.
Raines et al. (1992) *Eur J Biochem* 205:1053–1059.
Raines et al. (1999). J. Exp. Bot. 50:1–8.
Schimkat et al. (1990) *Planta* 181: 97–103.
Sheen et al. (1991) *The Plant Cell* 3: 225–245.
Shimamoto et al. (1989) *Nature* 338:274–276.
Stockhaus et al. (1989). *EMBO Journal* 8(9):2445–2451.
Truernit et al. (1995) *Planta* 196 (3):564–570.
Vasil et al. (1990) *Bio/Technology* 8:429–434.
Vasil et al. (1992) *Bio/Technology* 10:667–674.
Willingham et al., (1994) Plant Mol. Biol. 26:1191–1200
Woodrow (1982) *Methods Enzymol.* 90: 392–396.
Yamamoto et al. (1994) *Plant and Cell Physiology* 35(5): 773–778.
Yoo and Bowien (1995) *Current Microbiol.* 31: 55–61.

What is claimed is:

1. A method for improving the assimilation of carbon in a plant comprising the steps of:

(a) producing a transformed plant cell by inserting into the genome of a cell of a plant a nucleic acid construct comprising in the 5' to 3' direction, a promoter that functions in the cells of said plant, said promoter operably linked to a structural nucleic acid from *Chlorella sorokiniana* that encodes a sedoheptulose 1,7-bisphosphatase enzyme, said structural nucleic acid operably linked to a 3' non-translated nucleic acid that functions in said cells of said plant to cause transcriptional termination; and b) regenerating a transformed plant from said transformed plant cell wherein sedoheptulose 1,7-bisphosphatase enzyme is over expressed in cells of said plant.

2. A transformed plant with improved carbon assimilation which is the progeny of the transformed plant prepared by the method of claim 1, wherein the plant with improved carbon assimilation comprises the nucleic acid construct.

3. The transformed plant of claim 2 which is a corn plant.

* * * * *

SEQUENCE LISTING

<160> NUMBER OF SEQ ID NOS: 27

<210> SEQ ID NO 1
<211> LENGTH: 21
<212> TYPE: DNA
<213> ORGANISM: Artificial
<220> FEATURE:
<223> OTHER INFORMATION: synthetic primer

<400> SEQUENCE: 1
acatatgtgc gcgatcggcg a        21

<210> SEQ ID NO 2
<211> LENGTH: 25
<212> TYPE: DNA
<213> ORGANISM: Artificial
<220> FEATURE:
<223> OTHER INFORMATION: synthetic primer

<400> SEQUENCE: 2
ggatccagaa gaagattatt aggcg        25

<210> SEQ ID NO 3
<211> LENGTH: 966
<212> TYPE: DNA
<213> ORGANISM: Triticum aestivum

<400> SEQUENCE: 3
atgtgcgcga tcggcgacag cctggaggag ttcctgacca aggcgacgcc ggacaagaac        60
ctcatcaggc tgctgatctg catggggag gcgatgagga cgatcgcctt caaggtccgg        120
acggcctcct gcggcggcac ggcctgcgtc aactccttcg gcgacgagca gctcgccgtc        180
gacatgctcg ccgacaagct cctcttcgag gcgttggagt actcccatgt gtgcaagtac        240
gcgtgctctg aggaagtccc cgagctgcag gacatgggtg gcccggtcga aggtggattc        300
agtgtggcgt tcgacccct tgacggctcc agcatcgtgg acaccaactt caccgtggga        360
accatcttcg gcgtctggcc cggcgacaag ctgaccggcg tcaccggcgg tgaccaggtt        420
gctgccgcca tgggcatcta cggccctcgc accaccttcg tagttgccct caaggactgc        480
cccgggacac acgaattcct tctcctcgac gaaggtaaat ggcagcatgt caaggacacc        540
acgagcatcg gagaagggaa gatgttctcc cctggcaatc tgagggccac gttcgacaac        600
cctgattatg acaagcttgt caactactat gtgaaggaga agtacactct gcgttacacc        660
ggaggaatgg tccctgatgt caaccagatc atcgtgaagg agaagggcat cttcacgaac        720
gtgacgtcgc cgacggcgaa ggcgaagctg cggctgctgt tcgaggtggc gccgctgggg        780
ttcttgatag agaaggccgg cgggcacagc agcgacggca agcagtcggt gctgacaag        840 gtgatctccg tcctggacga gcggacccag gtggcctacg gctccaagaa cgagatcatc        900
cgcttcgagg agaccctcta cggctcctcc agactcgccg ccagcgccac cgtcggcgcc        960
accgcc        966

<210> SEQ ID NO 4
<211> LENGTH: 22
<212> TYPE: DNA
<213> ORGANISM: Artificial
<220> FEATURE:
<223> OTHER INFORMATION: synthetic primer -continued

<400> SEQUENCE: 4
ttcctcagag cacgcgtact tg                                              22

<210> SEQ ID NO 5
<211> LENGTH: 53
<212> TYPE: DNA
<213> ORGANISM: Artificial
<220> FEATURE:
<223> OTHER INFORMATION: adaptor primer

<400> SEQUENCE: 5
gggtcgacat tctagacaga attcgtggat ccttttttttt tttttttttt ttt           53

<210> SEQ ID NO 6
<211> LENGTH: 22
<212> TYPE: DNA
<213> ORGANISM: Artificial
<220> FEATURE:
<223> OTHER INFORMATION: synthetic primer

<400> SEQUENCE: 6
catgggagta ctccaacgcc tc                                              22

<210> SEQ ID NO 7
<211> LENGTH: 21
<212> TYPE: DNA
<213> ORGANISM: Artificial
<220> FEATURE:
<223> OTHER INFORMATION: adaptor primer

<400> SEQUENCE: 7
gggtcgacat tctagacaga a                                               21

<210> SEQ ID NO 8
<211> LENGTH: 1208
<212> TYPE: DNA
<213> ORGANISM: Triticum aestivum

<400> SEQUENCE: 8
tctagagcag caatggagac cgtcgcggct gccggctacg cccgcggggc cgccacgcgc      60
tccccggcgt gctgccgc catgtccttc tcgcagtcct acaggcccaa ggctgccagg       120
ccggcgacct cgttctacgg cgagtcgctg cgggcgaaca cggcgaggac gtcgttcccg     180
gcggggaggc agtccaaggc ggcgagccgg gcggcgctca ccaccggtg cgcgatcggc      240 gacagcctgg aggagttctt gaccaaggcg acgccggaca agaacctcat caggctgctg     300
atctgcatgg gggaggcgat gaggacgatc gccttcaagg tccggaccgc gtcctgcggc    360
ggcacggcct gcgtcaactc cttcggcgac gagcagctcg ccgtcgacat gctcgccgac     420
aagctcctct tcgaggcgtt ggagtactcc catgtgtgca agtacgcgtg ctctgaggaa     480
gtccccgagc tgcaggacat gggtggcccg gtcgaaggcg gattcagtgt ggcgttcgac     540
ccccttgacg gctccagcat cgtggacacc aacttcaccg tgggaaccat cttcggcgtc     600
tggcccggcg acaagctgac cggcgtcacc ggcggtgacc aggttgctgc cgccatgggc     660
atctacggcc ctcgcaccac cttcgtagtt gccctcaagg actgccccgg gacacacgaa     720
ttccttctcc tcgacgaagg taatggcag catgtcaagg acaccacgag catcggagaa    780
gggaagatgt tctcccttgg caatctgagg gccacgttcg acaaccctga ttatgacaag     840
cttgtcaact actatgtgaa ggagaagtac actctgcgtt acaccggagg aatggtccct    900
gatgtcaacc agatcatcgt gaaggagaag ggcatcttca cgaacgtgac gtcgccgacg     960

-continued

```
gcgaaggcga agctgcggct gctgttcgag gtggcgccgc tgggggttctt gatagagaag   1020 gccggcgggc acagcagcga cggcaagcag tcggtgctgg acaaggtgat ctccgtcctg   1080
gacgagcgga cccaggtggc ctacggctcc aagaacgaga tcatccgctt cgaggagacc   1140
ctctacggct cctccagact cgccgccagc gccaccgtcg cgccaccgc ctaataatct    1200 ttcttctg                                                            1208
```

<210> SEQ ID NO 9
<211> LENGTH: 322
<212> TYPE: PRT
<213> ORGANISM: Triticum aestivum

<400> SEQUENCE: 9

```
Met Cys Ala Ile Gly Asp Ser Leu Glu Glu Phe Leu Thr Lys Ala Thr
1               5                   10                  15

Pro Asp Lys Asn Leu Ile Arg Leu Leu Ile Cys Met Gly Glu Ala Met
            20                  25                  30

Arg Thr Ile Ala Phe Lys Val Arg Thr Ala Ser Cys Gly Gly Thr Ala
        35                  40                  45

Cys Val Asn Ser Phe Gly Asp Glu Gln Leu Ala Val Asp Met Leu Ala
    50                  55                  60

Asp Lys Leu Leu Phe Glu Ala Leu Glu Tyr Ser His Val Cys Lys Tyr
65                  70                  75                  80

Ala Cys Ser Glu Glu Val Pro Glu Leu Gln Asp Met Gly Gly Pro Val
                85                  90                  95

Glu Gly Gly Phe Ser Val Ala Phe Asp Pro Leu Asp Gly Ser Ser Ile
            100                 105                 110

Val Asp Thr Asn Phe Thr Val Gly Thr Ile Phe Gly Val Trp Pro Gly
        115                 120                 125

Asp Lys Leu Thr Gly Val Thr Gly Gly Asp Gln Val Ala Ala Ala Met
    130                 135                 140

Gly Ile Tyr Gly Pro Arg Thr Thr Phe Val Val Ala Leu Lys Asp Cys
145                 150                 155                 160

Pro Gly Thr His Glu Phe Leu Leu Leu Asp Glu Gly Lys Trp Gln His
                165                 170                 175

Val Lys Asp Thr Thr Ser Ile Gly Glu Gly Lys Met Phe Ser Pro Gly
            180                 185                 190

Asn Leu Arg Ala Thr Phe Asp Asn Pro Asp Tyr Asp Lys Leu Val Asn
        195                 200                 205

Tyr Tyr Val Lys Glu Lys Tyr Thr Leu Arg Tyr Thr Gly Gly Met Val
    210                 215                 220

Pro Asp Val Asn Gln Ile Ile Val Lys Glu Lys Gly Ile Phe Thr Asn
225                 230                 235                 240

Val Thr Ser Pro Thr Ala Lys Ala Lys Leu Arg Leu Leu Phe Glu Val
                245                 250                 255

Ala Pro Leu Gly Phe Leu Ile Glu Lys Ala Gly Gly His Ser Ser Asp
            260                 265                 270

Gly Lys Gln Ser Val Leu Asp Lys Val Ile Ser Val Leu Asp Glu Arg
        275                 280                 285

Thr Gln Val Ala Tyr Gly Ser Lys Asn Glu Ile Ile Arg Phe Glu Glu
    290                 295                 300

Thr Leu Tyr Gly Ser Ser Arg Leu Ala Ala Ser Ala Thr Val Gly Ala
305                 310                 315                 320

Thr Ala
```

```
<210> SEQ ID NO 10
<211> LENGTH: 17
<212> TYPE: DNA
<213> ORGANISM: Artificial
<220> FEATURE:
<223> OTHER INFORMATION: degenerate primer

<400> SEQUENCE: 10
ggacathtty gggttgg                                                  17

<210> SEQ ID NO 11
<211> LENGTH: 18
<212> TYPE: DNA
<213> ORGANISM: Artificial
<220> FEATURE:
<223> OTHER INFORMATION: synthetic primer

<400> SEQUENCE: 11
rtackargtr tayttytc                                                 18

<210> SEQ ID NO 12
<211> LENGTH: 382
<212> TYPE: PRT
<213> ORGANISM: Chlorella sorokiniana

<400> SEQUENCE: 12
```

| Met | Gln | Ala | Thr | Ala | Val | Ala | Thr | Ala | Ala | Pro | Ala | Ala | Arg | Val | Ala |
|---|---|---|---|---|---|---|---|---|---|---|---|---|---|---|---|
| 1 | | | | 5 | | | | | 10 | | | | | 15 | |

| Thr | Thr | Gly | Lys | Ala | Ala | Thr | Gly | Val | Lys | Ala | Ala | Pro | Arg | Val | Ala |
|---|---|---|---|---|---|---|---|---|---|---|---|---|---|---|---|
| | | | 20 | | | | | 25 | | | | | 30 | | |

| Val | Arg | Ala | Ala | Gly | Ala | Ser | Ala | Ser | Ser | Ser | Phe | Ala | Thr | Gly | Ala |
|---|---|---|---|---|---|---|---|---|---|---|---|---|---|---|---|
| | | 35 | | | | | 40 | | | | | 45 | | | |

| Arg | Leu | Ser | Lys | Ala | Ser | Arg | Thr | Ala | Ala | Arg | Ala | Ala | Val | Ala |
|---|---|---|---|---|---|---|---|---|---|---|---|---|---|---|
| | 50 | | | | | 55 | | | | | 60 | | | |

| Ala | Gln | Ala | Lys | Ile | Gly | Asp | Thr | Leu | Glu | Glu | Phe | Leu | Leu | Glu | Ala |
|---|---|---|---|---|---|---|---|---|---|---|---|---|---|---|---|
| 65 | | | | | 70 | | | | | 75 | | | | | 80 |

| Thr | Pro | Asp | Pro | Lys | Leu | Arg | Gln | Leu | Met | Met | Ser | Met | Ser | Glu | Ala |
|---|---|---|---|---|---|---|---|---|---|---|---|---|---|---|---|
| | | | | 85 | | | | | 90 | | | | | 95 | |

| Ile | Arg | Thr | Ile | Ala | Tyr | Lys | Val | Arg | Thr | Ala | Ser | Cys | Gly | Gly | Thr |
|---|---|---|---|---|---|---|---|---|---|---|---|---|---|---|---|
| | | | 100 | | | | | 105 | | | | | 110 | | |

| Ala | Cys | Val | Asn | Ser | Phe | Gly | Asp | Glu | Gln | Leu | Ala | Val | Asp | Leu | Leu |
|---|---|---|---|---|---|---|---|---|---|---|---|---|---|---|---|
| | | 115 | | | | | 120 | | | | | 125 | | | |

| Ala | Asp | Lys | Leu | Leu | Phe | Glu | Ala | Leu | Lys | Tyr | Ser | Gly | Cys | Cys | Lys |
|---|---|---|---|---|---|---|---|---|---|---|---|---|---|---|---|
| | 130 | | | | | 135 | | | | | 140 | | | | |

| Leu | Ala | Cys | Ser | Glu | Glu | Val | Pro | Glu | Pro | Leu | Asp | Leu | Gly | Gly | Glu |
|---|---|---|---|---|---|---|---|---|---|---|---|---|---|---|---|
| 145 | | | | | 150 | | | | | 155 | | | | | 160 |

| Gly | Phe | Ser | Val | Ala | Phe | Asp | Pro | Leu | Asp | Gly | Ser | Ser | Ile | Val | Asp |
|---|---|---|---|---|---|---|---|---|---|---|---|---|---|---|---|
| | | | | 165 | | | | | 170 | | | | | 175 | |

| Thr | Asn | Phe | Ser | Val | Gly | Thr | Ile | Phe | Gly | Val | Trp | Pro | Gly | Asp | Lys |
|---|---|---|---|---|---|---|---|---|---|---|---|---|---|---|---|
| | | | 180 | | | | | 185 | | | | | 190 | | |

| Leu | Thr | Gly | Ile | Thr | Gly | Arg | Gln | Gln | Ala | Ala | Ala | Gly | Met | Gly | Ile |
|---|---|---|---|---|---|---|---|---|---|---|---|---|---|---|---|
| | | 195 | | | | | 200 | | | | | 205 | | | |

| Tyr | Gly | Pro | Arg | Thr | Val | Phe | Cys | Ile | Ala | Leu | Lys | Asp | Ala | Pro | Gly |
|---|---|---|---|---|---|---|---|---|---|---|---|---|---|---|---|
| | 210 | | | | | 215 | | | | | 220 | | | | |

| Cys | His | Glu | Phe | Leu | Leu | Gln | Asp | Asp | Gly | Lys | Trp | Leu | His | Val | Lys |
|---|---|---|---|---|---|---|---|---|---|---|---|---|---|---|---|
| 225 | | | | | 230 | | | | | 235 | | | | | 240 |

| Glu | Thr | Glu | Thr | Ile | Gly | Glu | Gly | Lys | Met | Phe | Ser | Pro | Gly | Asn | Leu |
|---|---|---|---|---|---|---|---|---|---|---|---|---|---|---|---|
| | | | | 245 | | | | | 250 | | | | | 255 | |

```
Arg Ala Thr Phe Asp Asn Pro Ala Tyr Glu Lys Leu Ile Ala Tyr Tyr
            260                 265                 270

Ile Gly Glu Lys Tyr Thr Leu Arg Tyr Thr Gly Gly Met Val Pro Asp
        275                 280                 285

Val Phe Gln Ile Ile Val Lys Glu Lys Gly Val Phe Thr Asn Val Ile
    290                 295                 300

Ser Pro Ser Thr Lys Ala Lys Leu Arg Leu Leu Phe Glu Val Ala Pro
305                 310                 315                 320

Leu Ala Leu Leu Val Glu Lys Ala Gly Gly Ala Ser Ser Cys Asp Gly
                325                 330                 335

Leu Cys Val Ser Gly Leu Asp Val Glu Val Lys Gln His Asp Gln Arg
            340                 345                 350

Thr Gln Ile Cys Tyr Gly Ser Lys Gly Glu Val Arg Arg Phe Glu Glu
        355                 360                 365

Tyr Met Tyr Gly Asn Ser Pro Arg Phe Ser Glu Val Thr Ala
    370                 375                 380
```

<210> SEQ ID NO 13
<211> LENGTH: 22
<212> TYPE: DNA
<213> ORGANISM: Artificial
<220> FEATURE:
<223> OTHER INFORMATION: synthetic primer

<400> SEQUENCE: 13
gatggtctcg gtctccttca cg                                            22

<210> SEQ ID NO 14
<211> LENGTH: 18
<212> TYPE: DNA
<213> ORGANISM: Artificial
<220> FEATURE:
<223> OTHER INFORMATION: synthetic primer

<400> SEQUENCE: 14
cagccacttg ccatcgtc                                                 18

<210> SEQ ID NO 15
<211> LENGTH: 22
<212> TYPE: DNA
<213> ORGANISM: Artificial
<220> FEATURE:
<223> OTHER INFORMATION: synthetic primer

<400> SEQUENCE: 15
gatggtctcg gtctccttca cg                                            22

<210> SEQ ID NO 16
<211> LENGTH: 22
<212> TYPE: DNA
<213> ORGANISM: Artificial
<220> FEATURE:
<223> OTHER INFORMATION: synthetic primer

<400> SEQUENCE: 16
tcctcagagc acgccagctt gc                                            22

<210> SEQ ID NO 17
<211> LENGTH: 24
<212> TYPE: DNA
<213> ORGANISM: Artificial
<220> FEATURE:
<223> OTHER INFORMATION: synthetic primer

```
<400> SEQUENCE: 17
agctgctcat cgccgaacga gttg                                              24

<210> SEQ ID NO 18
<211> LENGTH: 22
<212> TYPE: DNA
<213> ORGANISM: Artificial
<220> FEATURE:
<223> OTHER INFORMATION: synthetic primer

<400> SEQUENCE: 18
agttcctgct gcaggacgat gg                                                22

<210> SEQ ID NO 19
<211> LENGTH: 23
<212> TYPE: DNA
<213> ORGANISM: Artificial
<220> FEATURE:
<223> OTHER INFORMATION: synthetic primer

<400> SEQUENCE: 19
cccagtcacg acgttgtaaa acg                                               23

<210> SEQ ID NO 20
<211> LENGTH: 1460
<212> TYPE: DNA
<213> ORGANISM: Chlorella sorokiniana

<400> SEQUENCE: 20
gccggttgat cctcgagctc caaggcactc gggcacgatg caggccaccg ctgtcgccac        60
cgccgcccct gcggcccgcg tcgccaccac tggcaaggcc gccaccggcg tcaaggccgc       120
cccccgcgtg gccgtgcgcg ccgccggcgc cagcgccagc agcagctttg ccaccggcgc       180
ccgcctgagc gccaaggcca gccgcaccgc cgcccgccgc gccgcggtgg ccgcccaggc       240
caagatcggc gacacgctgg aggagttcct gctggaggcc accccgacc ccaagctgcg        300 ccagctcatg atgtccatgt ccgaggccat ccgcaccatc gcctacaagg tgcgcaccgc       360
ctcgtgcggc ggcaccgcct gcgtcaactc gttcggcgat gagcagctgg ccgtcgacct       420
gctggccgac aagctgctgt cgaggcccct caagtactct ggctgttgca agctggcgtg       480
ctctgaggag gtgcctgagc ccctggacct gggcggcgag ggcttctccg tggcatttga       540
ccccctggac ggctcctcca tcgtggacac caacttctct gtgggcacga tatttgggt       600 gtggcccggc gacaagctga ccggcatcac gggccgccag caggccgccg ccggcatggg       660
catctacggc ccccgcaccg tcttctgcat cgccctcaag gacgcccccg gctgccacga       720
gttcctgctg caggacgatg gcaagtggct gcacgtgaag gagaccgaga ccatcggcga       780
gggcaagatg ttctcccccg gcaacctgcg cgccaccttt gacaaccccg cgtacgagaa       840
gctgatcgcc tactacatcg gcgagaagta cacgctgcgc tacaccggcg gcatggtgcc       900
cgacgtgttc cagatcatcg tgaaggagaa gggcgtgttc accaacgtca tctcccccctc      960 caccaaggcc aagctgcgcc tgctgttcga ggtggcgccc ctggccctgc tggttgagaa      1020
ggcaggcggc gcctcctcct gcgacggcct gtgcgtgagc ggcctggacg tggaggtcaa      1080
gcagcacgac cagcgcaccc agatctgcta tggctccaag ggcgaggtgc ggcggttttga    1140 ggagtacatg tacggcaact ccccccgctt ctccgaggtc accgcctaag cggctggtca      1200
tcgcctgagc ggctcagtgc tgctgactat gcagccggcg gctgactatg ctggtcttaa      1260
cctgagcggc tggccgtcaa acgctggcta gcagcgccgc cccctgagca gcctcggaga      1320
```

-continued

| ctcccgccgg ctggcctatt caagctggct ggcgccggag ctccgcctgc cctggttgca | 1380 |
| cccaccattc gcttgctccc ccctccgcgc tttcatcatg tgctttccgc ccgcaacgcc | 1440 |
| ctgtccaatt cattcattat | 1460 |

<210> SEQ ID NO 21
<211> LENGTH: 55
<212> TYPE: DNA
<213> ORGANISM: Artificial
<220> FEATURE:
<223> OTHER INFORMATION: synthetic primer

<400> SEQUENCE: 21

| aaggtgcgca ccgcctcgtc cggcggcacc gcctccgtca actcgttcgg cgatg | 55 |

<210> SEQ ID NO 22
<211> LENGTH: 1460
<212> TYPE: DNA
<213> ORGANISM: Chlorella sorokiniana

<400> SEQUENCE: 22

| gccggttgat cctcgagctc caaggcactc gggcacgatg caggccaccg ctgtcgccac | 60 |
| cgccgcccct gcggcccgcg tcgccaccac tggcaaggcc gccaccggcg tcaaggccgc | 120 |
| cccccgcgtg gccgtgcgcg ccgcggcgc cagcgccagc agcagctttg ccaccggcgc | 180 |
| ccgcctgagc gccaaggcca ccgcaccgc cgcccgccgc gccgccgtgg ccgcccaggc | 240 |
| caagatcggc gacacgctgg aggagttcct gctggaggcc accccgacc ccaagctgcg | 300 |
| ccagctcatg atgtccatgt ccgaggccat ccgcaccatc gcctacaagg tgcgcaccgc | 360 |
| ctcgtccggc ggcaccgcct ccgtcaactc gttcggcgat gagcagctgg ccgtcgacct | 420 |
| gctggccgac aagctgctgt cgaggcccct caagtactct ggctgttgca agctggcgtg | 480 |
| ctctgaggag gtgcctgagc ccctggacct gggcggcgag ggcttctccg tggcatttga | 540 |
| cccccctggac ggctcctcca tcgtggacac caacttctct gtgggcacga tatttggggt | 600 |
| gtggcccggc gacaagctga ccggcatcac gggccgccag caggccgccg ccggcatggg | 660 |
| catctacggc cccgcaccg tcttctgcat cgccctcaag gacgcccccg gctgccacga | 720 |
| gttcctgctg caggacgatg gcaagtggct gcacgtgaag gagaccgaga ccatcggcga | 780 |
| gggcaagatg ttctcccccg gcaacctgcg cgccacctt gacaacccg cgtacgagaa | 840 |
| gctgatcgcc tactacatcg gcgagaagta cacgctgcgc tacaccggcg gcatggtgcc | 900 |
| cgacgtgttc cagatcatcg tgaaggagaa gggcgtgttc accaacgtca tctccccctc | 960 |
| caccaaggcc aagctgcgcc tgctgttcga ggtggcgccc ctggccctgc tggttgagaa | 1020 |
| ggcaggcggc gcctcctcct gcgacggcct gtgcgtgagc ggcctggacg tggaggtcaa | 1080 |
| gcagcacgac cagcgcaccc agatctgcta tggctccaag ggcgaggtgc ggcggtttga | 1140 |
| ggagtacatg tacggcaact ccccccgctt ctccgaggtc accgcctaag cggctggtca | 1200 |
| tcgcctgagc ggctcagtgc tgctgactat gcagccggcg gctgactatg ctggtcttaa | 1260 |
| cctgagcggc tggccgtcaa acgctggcta gcagcgccgc ccctgagca gcctcggaga | 1320 |
| ctcccgccgg ctggcctatt caagctggct ggcgccggag ctccgcctgc cctggttgca | 1380 |
| cccaccattc gcttgctccc ccctccgcgc tttcatcatg tgctttccgc ccgcaacgcc | 1440 |
| ctgtccaatt cattcattat | 1460 |

<210> SEQ ID NO 23
<211> LENGTH: 383
<212> TYPE: PRT
<213> ORGANISM: Chlorella sorokiniana

<400> SEQUENCE: 23

```
Met Gln Ala Thr Ala Val Ala Thr Ala Ala Pro Ala Ala Arg Val Ala
1               5                   10                  15

Thr Thr Gly Lys Ala Ala Thr Gly Val Lys Ala Ala Pro Arg Val Ala
            20                  25                  30

Val Arg Ala Ala Gly Ala Ser Ala Ser Ser Ser Phe Ala Thr Gly Ala
        35                  40                  45

Arg Leu Ser Ala Lys Ala Ser Arg Thr Ala Ala Arg Ala Ala Val
    50                  55                  60

Ala Ala Gln Ala Lys Ile Gly Asp Thr Leu Glu Glu Phe Leu Leu Glu
65                  70                  75                  80

Ala Thr Pro Asp Pro Lys Leu Arg Gln Leu Met Met Ser Met Ser Glu
                85                  90                  95

Ala Ile Arg Thr Ile Ala Tyr Lys Val Arg Thr Ala Ser Ser Gly Gly
            100                 105                 110

Thr Ala Ser Val Asn Ser Phe Gly Asp Glu Gln Leu Ala Val Asp Leu
        115                 120                 125

Leu Ala Asp Lys Leu Leu Phe Glu Ala Leu Lys Tyr Ser Gly Cys Cys
    130                 135                 140

Lys Leu Ala Cys Ser Glu Glu Val Pro Glu Pro Leu Asp Leu Gly Gly
145                 150                 155                 160

Glu Gly Phe Ser Val Ala Phe Asp Pro Leu Asp Gly Ser Ser Ile Val
                165                 170                 175

Asp Thr Asn Phe Ser Val Gly Thr Ile Phe Gly Val Trp Pro Gly Asp
            180                 185                 190

Lys Leu Thr Gly Ile Thr Gly Arg Gln Gln Ala Ala Ala Gly Met Gly
        195                 200                 205

Ile Tyr Gly Pro Arg Thr Val Phe Cys Ile Ala Leu Lys Asp Ala Pro
    210                 215                 220

Gly Cys His Glu Phe Leu Leu Gln Asp Asp Gly Lys Trp Leu His Val
225                 230                 235                 240

Lys Glu Thr Glu Thr Ile Gly Glu Gly Lys Met Phe Ser Pro Gly Asn
                245                 250                 255

Leu Arg Ala Thr Phe Asp Asn Pro Ala Tyr Glu Lys Leu Ile Ala Tyr
            260                 265                 270

Tyr Ile Gly Glu Lys Tyr Thr Leu Arg Tyr Thr Gly Gly Met Val Pro
        275                 280                 285

Asp Val Phe Gln Ile Ile Val Lys Glu Lys Gly Val Phe Thr Asn Val
    290                 295                 300

Ile Ser Pro Ser Thr Lys Ala Lys Leu Arg Leu Leu Phe Glu Val Ala
305                 310                 315                 320

Pro Leu Ala Leu Leu Val Glu Lys Ala Gly Gly Ala Ser Ser Cys Asp
                325                 330                 335

Gly Leu Cys Val Ser Gly Leu Asp Val Glu Val Lys Gln His Asp Gln
            340                 345                 350

Arg Thr Gln Ile Cys Tyr Gly Ser Lys Gly Glu Val Arg Arg Phe Glu
        355                 360                 365

Glu Tyr Met Tyr Gly Asn Ser Pro Arg Phe Ser Glu Val Thr Ala
    370                 375                 380
```

<210> SEQ ID NO 24
<211> LENGTH: 389
<212> TYPE: PRT
<213> ORGANISM: Chlamydomonas reinhardtii

<400> SEQUENCE: 24

```
Met Ala Ala Met Met Arg Gln Lys Val Ala Gly Ala Ile Ala Gly
1               5                   10                  15

Glu Arg Arg Ser Ala Val Ala Pro Lys Met Gly Arg Ala Ala Thr Ala
            20                  25                  30

Pro Val Val Ala Ser Ala Asn Ala Ser Ala Phe Lys Gly Ala Ala
        35                  40                  45

Val Thr Ala Arg Val Lys Ala Ser Thr Arg Ala Ala Arg Val Gln Ser
    50                  55                  60

Arg Arg Thr Ala Val Leu Thr Gln Ala Lys Ile Gly Asp Ser Leu Ala
65                  70                  75                  80

Glu Phe Leu Val Glu Ala Thr Pro Asp Pro Lys Leu Arg His Val Met
                85                  90                  95

Met Ser Met Ala Glu Ala Thr Arg Thr Ile Ala His Lys Val Arg Thr
            100                 105                 110

Ala Ser Cys Ala Gly Thr Ala Cys Val Asn Ser Phe Gly Asp Glu Gln
        115                 120                 125

Leu Ala Val Asp Met Val Ala Asp Lys Leu Leu Phe Glu Ala Leu Lys
    130                 135                 140

Tyr Ser His Val Cys Lys Leu Ala Cys Ser Glu Glu Val Pro Glu Pro
145                 150                 155                 160

Val Asp Met Gly Gly Glu Gly Phe Cys Val Ala Phe Asp Pro Leu Asp
                165                 170                 175

Gly Ser Ser Ser Asp Thr Asn Phe Ala Val Gly Thr Ile Phe Gly
            180                 185                 190

Val Trp Pro Gly Asp Lys Leu Thr Asn Ile Thr Gly Arg Glu Gln Val
        195                 200                 205

Ala Ala Gly Met Gly Ile Tyr Gly Pro Arg Thr Val Phe Cys Ile Ala
    210                 215                 220

Leu Lys Asp Ala Pro Gly Cys His Glu Phe Leu Leu Met Asp Asp Gly
225                 230                 235                 240

Lys Trp Met His Val Lys Glu Thr Thr His Ile Gly Glu Gly Lys Met
                245                 250                 255

Phe Ala Pro Gly Asn Leu Arg Ala Thr Phe Asp Asn Pro Ala Tyr Glu
            260                 265                 270

Arg Leu Ile Asn Phe Tyr Leu Gly Glu Lys Tyr Thr Leu Arg Tyr Thr
        275                 280                 285

Gly Gly Ile Val Pro Asp Leu Phe Gln Ile Ile Val Lys Glu Lys Gly
    290                 295                 300

Val Phe Thr Asn Leu Thr Ser Pro Thr Thr Lys Ala Lys Leu Arg Ile
305                 310                 315                 320

Leu Phe Glu Val Ala Pro Leu Ala Leu Leu Ile Glu Lys Ala Gly Gly
                325                 330                 335

Ala Ser Ser Cys Asp Gly Lys Ala Val Ser Ala Leu Asp Ile Pro Ile
            340                 345                 350

Leu Val Cys Asp Gln Arg Thr Gln Ile Cys Tyr Gly Ser Ile Gly Glu
        355                 360                 365
```

Val Arg Arg Phe Glu Glu Tyr Met Tyr Gly Thr Ser Pro Arg Phe Ser
    370                 375                 380

Glu Lys Val Val Ala
385

<210> SEQ ID NO 25
<211> LENGTH: 387
<212> TYPE: PRT
<213> ORGANISM: Spinacia oleracea

<400> SEQUENCE: 25

Met Glu Thr Ser Met Ala Cys Cys Ser Arg Ser Ile Val Leu Pro Arg
1               5                   10                  15

Val Ser Pro Gln His Ser Ser Ala Leu Val Pro Ser Ser Ile Asn Leu
            20                  25                  30

Lys Ser Leu Lys Ser Ser Leu Phe Gly Glu Ser Leu Arg Met Thr
        35                  40                  45

Thr Lys Ser Ser Val Arg Val Asn Lys Ala Lys Asn Ser Ser Leu Val
    50                  55                  60

Thr Lys Cys Glu Leu Gly Asp Ser Leu Glu Glu Phe Leu Ala Lys Ala
65                  70                  75                  80

Thr Thr Asp Lys Gly Leu Ile Arg Leu Met Met Cys Met Gly Glu Ala
                85                  90                  95

Leu Arg Thr Ile Gly Phe Lys Val Arg Thr Ala Ser Cys Gly Gly Thr
            100                 105                 110

Gln Cys Val Asn Thr Phe Gly Asp Glu Gln Leu Ala Ile Asp Val Leu
        115                 120                 125

Ala Asp Lys Leu Leu Phe Glu Ala Leu Asn Tyr Ser His Phe Cys Lys
130                 135                 140

Tyr Ala Cys Ser Glu Glu Leu Pro Glu Leu Gln Asp Met Gly Gly Pro
145                 150                 155                 160

Val Asp Gly Gly Phe Ser Val Ala Phe Asp Pro Leu Asp Gly Ser Ser
                165                 170                 175

Ile Val Asp Thr Asn Phe Ser Val Gly Thr Ile Phe Gly Val Trp Pro
            180                 185                 190

Gly Asp Lys Leu Thr Gly Val Thr Gly Arg Asp Gln Val Ala Ala Ala
        195                 200                 205

Met Gly Ile Tyr Gly Pro Arg Thr Thr Tyr Val Leu Ala Leu Lys Asp
210                 215                 220

Tyr Pro Gly Thr His Glu Phe Leu Leu Leu Asp Glu Gly Lys Trp Gln
225                 230                 235                 240

His Val Lys Glu Thr Thr Glu Ile Asn Glu Gly Lys Leu Phe Cys Pro
                245                 250                 255

Gly Asn Leu Arg Ala Thr Ser Asp Asn Ala Asp Tyr Ala Lys Leu Ile
            260                 265                 270

Gln Tyr Tyr Ile Lys Glu Lys Tyr Thr Leu Arg Tyr Thr Gly Gly Met
        275                 280                 285

Val Pro Asp Val Asn Gln Ile Ile Val Lys Glu Lys Gly Ile Phe Thr
290                 295                 300

Asn Val Ile Ser Pro Thr Ala Lys Ala Lys Leu Arg Leu Leu Phe Glu
305                 310                 315                 320

Val Ala Pro Leu Gly Phe Leu Ile Glu Lys Ala Gly Gly His Ser Ser
                325                 330                 335

Glu Gly Thr Lys Ser Val Leu Asp Ile Glu Val Lys Asn Leu Asp Asp
            340                 345                 350

Arg Thr Gln Val Ala Tyr Gly Ser Leu Asn Glu Ile Ile Arg Phe Glu
            355                 360                 365

Lys Thr Leu Tyr Gly Ser Ser Arg Leu Glu Glu Pro Val Pro Val Gly
    370                 375                 380

Ala Ala Ala
385

<210> SEQ ID NO 26
<211> LENGTH: 393
<212> TYPE: PRT
<213> ORGANISM: Arabidopsis thaliana

<400> SEQUENCE: 26

Met Glu Thr Ser Ile Ala Cys Tyr Ser Arg Gly Ile Leu Pro Pro Ser
1               5                   10                  15

Val Ser Ser Gln Arg Ser Ser Thr Leu Val Ser Pro Ser Tyr Ser
            20                  25                  30

Thr Ser Ser Ser Phe Lys Arg Leu Lys Ser Ser Ile Phe Gly Asp
            35                  40                  45

Ser Leu Arg Leu Ala Pro Lys Ser Gln Leu Lys Ala Thr Lys Ala Lys
    50                  55                  60

Ser Asn Gly Ala Ser Thr Val Thr Lys Cys Glu Ile Gly Gln Ser Leu
65                  70                  75                  80

Glu Glu Phe Leu Ala Gln Ala Thr Pro Asp Lys Gly Leu Arg Thr Leu
                85                  90                  95

Leu Met Cys Met Gly Glu Ala Leu Arg Thr Ile Ala Phe Lys Val Arg
            100                 105                 110

Thr Ala Ser Cys Gly Gly Thr Ala Cys Val Asn Ser Phe Gly Asp Glu
        115                 120                 125

Gln Leu Ala Val Asp Met Leu Ala Asp Lys Leu Leu Phe Glu Ala Leu
    130                 135                 140

Gln Tyr Ser His Val Cys Lys Tyr Ala Cys Ser Glu Glu Val Pro Glu
145                 150                 155                 160

Leu Gln Asp Met Gly Gly Pro Val Glu Gly Gly Phe Ser Val Ala Phe
                165                 170                 175

Asp Pro Leu Asp Gly Ser Ser Ile Val Asp Thr Asn Phe Thr Val Gly
            180                 185                 190

Thr Ile Phe Gly Val Trp Pro Gly Asp Lys Leu Thr Gly Ile Thr Gly
        195                 200                 205

Gly Asp Gln Val Ala Ala Ala Met Gly Ile Tyr Gly Pro Arg Thr Thr
    210                 215                 220

Tyr Val Leu Ala Val Lys Gly Phe Pro Gly Thr His Glu Phe Leu Leu
225                 230                 235                 240

Leu Asp Glu Gly Lys Trp Gln His Val Lys Glu Thr Thr Glu Ile Ala
                245                 250                 255

Glu Gly Lys Met Phe Ser Pro Gly Asn Leu Arg Ala Thr Phe Asp Asn
            260                 265                 270

Ser Glu Tyr Ser Lys Leu Ile Asp Tyr Val Lys Glu Lys Tyr Thr
        275                 280                 285

Leu Arg Tyr Thr Gly Gly Met Val Pro Asp Val Asn Gln Ile Ile Val
    290                 295                 300

Lys Glu Lys Gly Ile Phe Thr Asn Val Thr Ser Pro Thr Ala Lys Ala
305                 310                 315                 320

Lys Leu Arg Leu Leu Phe Glu Val Ala Pro Leu Gly Leu Leu Ile Glu
                325                 330                 335

Asn Ala Gly Gly Phe Ser Ser Asp Gly His Lys Ser Val Leu Asp Lys
            340                 345                 350

Thr Ile Ile Asn Leu Asp Asp Arg Thr Gln Val Ala Tyr Gly Ser Lys
            355                 360                 365

Asn Glu Ile Ile Arg Phe Glu Glu Thr Leu Tyr Gly Thr Ser Arg Leu
            370                 375                 380

Lys Asn Val Pro Ile Gly Val Thr Ala
385                 390

<210> SEQ ID NO 27
<211> LENGTH: 393
<212> TYPE: PRT
<213> ORGANISM: Triticum aestivum

<400> SEQUENCE: 27

Met Glu Thr Val Ala Ala Ala Gly Tyr Ala His Gly Ala Ala Thr Arg
1               5                   10                  15

Ser Pro Ala Cys Cys Ala Ala Met Ser Phe Ser Gln Ser Tyr Arg Pro
            20                  25                  30

Lys Ala Ala Arg Pro Ala Thr Ser Phe Tyr Gly Glu Ser Leu Arg Ala
            35                  40                  45

Asn Thr Ala Arg Thr Ser Phe Pro Ala Gly Arg Gln Ser Lys Ala Ala
            50                  55                  60

Ser Arg Ala Ala Leu Thr Thr Arg Cys Ala Ile Gly Asp Ser Leu Glu
65                  70                  75                  80

Glu Phe Leu Thr Lys Ala Thr Pro Asp Lys Asn Leu Ile Arg Leu Leu
                85                  90                  95

Ile Cys Met Gly Glu Ala Met Arg Thr Ile Ala Phe Lys Val Arg Thr
            100                 105                 110

Ala Ser Cys Gly Gly Thr Ala Cys Val Asn Ser Phe Gly Asp Glu Gln
            115                 120                 125

Leu Ala Val Asp Met Leu Ala Asp Lys Leu Leu Phe Glu Ala Leu Glu
            130                 135                 140

Tyr Ser His Val Cys Lys Tyr Ala Cys Ser Glu Glu Val Pro Glu Leu
145                 150                 155                 160

Gln Asp Met Gly Gly Pro Val Glu Gly Phe Ser Val Ala Phe Asp
                165                 170                 175

Pro Leu Asp Gly Ser Ser Ile Val Asp Thr Asn Phe Thr Val Gly Thr
            180                 185                 190

Ile Phe Gly Val Trp Pro Gly Asp Lys Leu Thr Gly Val Thr Gly Gly
            195                 200                 205

Asp Gln Val Ala Ala Met Gly Ile Tyr Gly Pro Arg Thr Thr Phe
            210                 215                 220

Val Val Ala Leu Lys Asp Cys Pro Gly Thr His Glu Phe Leu Leu Leu
225                 230                 235                 240

Asp Glu Gly Lys Trp Gln His Val Lys Asp Thr Ser Ile Gly Glu
                245                 250                 255

Gly Lys Met Phe Ser Pro Gly Asn Leu Arg Ala Thr Phe Asp Asn Pro
            260                 265                 270

Asp Tyr Asp Lys Leu Val Asn Tyr Val Lys Glu Lys Tyr Thr Leu
            275                 280                 285

Arg Tyr Thr Gly Gly Met Val Pro Asp Val Asn Gln Ile Ile Val Lys
            290                 295                 300

Glu Lys Gly Ile Phe Thr Asn Val Thr Ser Pro Thr Ala Lys Ala Lys
305                 310                 315                 320

-continued

```
Leu Arg Leu Leu Phe Glu Val Ala Pro Leu Gly Phe Leu Ile Glu Lys
            325                 330                 335

Ala Gly Gly His Ser Ser Asp Gly Lys Gln Ser Val Leu Asp Lys Val
            340                 345                 350

Ile Ser Val Leu Asp Glu Arg Thr Gln Val Ala Tyr Gly Ser Lys Asn
        355                 360                 365

Glu Ile Ile Arg Phe Glu Thr Leu Tyr Gly Ser Ser Arg Leu Ala
    370                 375                 380

Ala Ser Ala Thr Val Gly Ala Thr Ala
385                 390
```